United States Patent
Ghosh et al.

(10) Patent No.: US 10,330,663 B2
(45) Date of Patent: Jun. 25, 2019

(54) SYSTEM AND METHOD FOR MEASURING SEPARATION RATE OF WATER FROM WATER-IN-CRUDE OIL EMULSIONS

(71) Applicants: Phillips 66 Company, Houston, TX (US); Board of Regents of the University of Oklahoma, Norman, OK (US)

(72) Inventors: Moniraj Ghosh, Bartlesville, OK (US); Brian P. Grady, Norman, OK (US); Jeffrey H. Harwell, Norman, OK (US); James A. Miles, Norman, OK (US)

(73) Assignees: PHILLIPS 66 COMPANY, Houston, TX (US); BOARD OF REGENTS OF THE UNIVERSITY OF OKLAHOMA, Norman, OK (US)

(*) Notice: Subject to any disclaimer, the term of this patent is extended or adjusted under 35 U.S.C. 154(b) by 887 days.

(21) Appl. No.: 14/802,136

(22) Filed: Jul. 17, 2015

(65) Prior Publication Data
US 2016/0047792 A1 Feb. 18, 2016

Related U.S. Application Data

(60) Provisional application No. 62/036,301, filed on Aug. 12, 2014.

(51) Int. Cl.
  *G01N 33/26* (2006.01)
  *G01N 33/28* (2006.01)
(52) U.S. Cl.
  CPC ................. *G01N 33/2847* (2013.01)
(58) Field of Classification Search
  CPC .................................................. G01N 33/2847
  See application file for complete search history.

(56) References Cited

U.S. PATENT DOCUMENTS

| | | | | |
|---|---|---|---|---|
| 2002/0166803 | A1* | 11/2002 | Mazurek | B01D 17/005 210/86 |
| 2014/0008304 | A1* | 1/2014 | Jansen | B01D 17/12 210/708 |
| 2014/0090454 | A1* | 4/2014 | Surman | G01N 27/023 73/61.61 |

OTHER PUBLICATIONS

Van Dijk, et al., *Ch. 19: Monitoring the demulsification of crude oil emulsions by using conductivity measurements*, Emulsions and Emulsion Stability; Surfactant Science (CRC Press, 2d ed. 2006) 651-662.

Kostoglou, et al., *Evolution of volume fractions and droplet sizes by analysis of electrical conductance curves during destabilization of oil-in-water emulsions*, J. Colloid Interface Sci. 394(1) (2010) 408-416.

* cited by examiner

*Primary Examiner* — Son T Le
*Assistant Examiner* — Alex T Devito
(74) *Attorney, Agent, or Firm* — Chris P. Perque; Adams and Reese LLP

(57) ABSTRACT

System and method relates to measuring separation rate of water from water-in-crude oil emulsions at elevated temperature. The system includes an electrolytic interface (conductivity) cell comprising a plurality of capacitance/conductance probes disposed at different heights in a fluid stream disposed within the interface cell and an analyzer. Logic of the analyzer determines the separation rate based on signals received from the plurality of capacitance/conductance probes in the interface cell that are coupled to monitor the fluid stream. Methods for making and using the system are also disclosed.

30 Claims, 32 Drawing Sheets

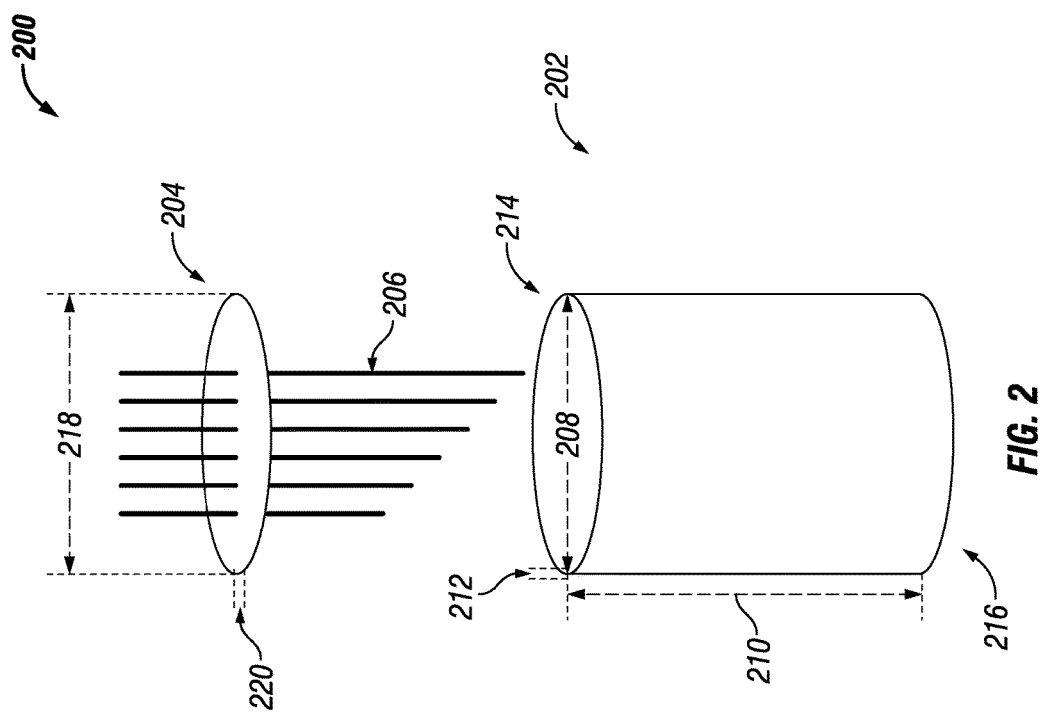

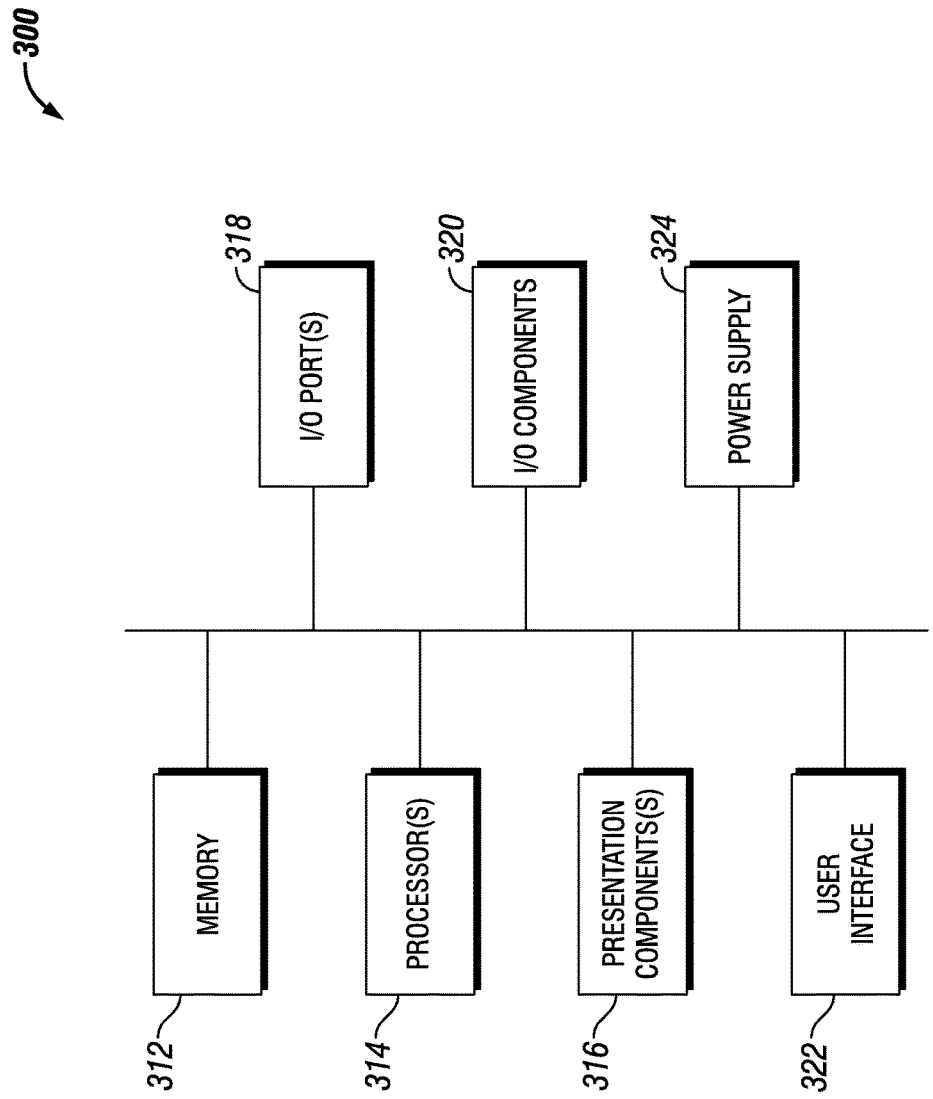

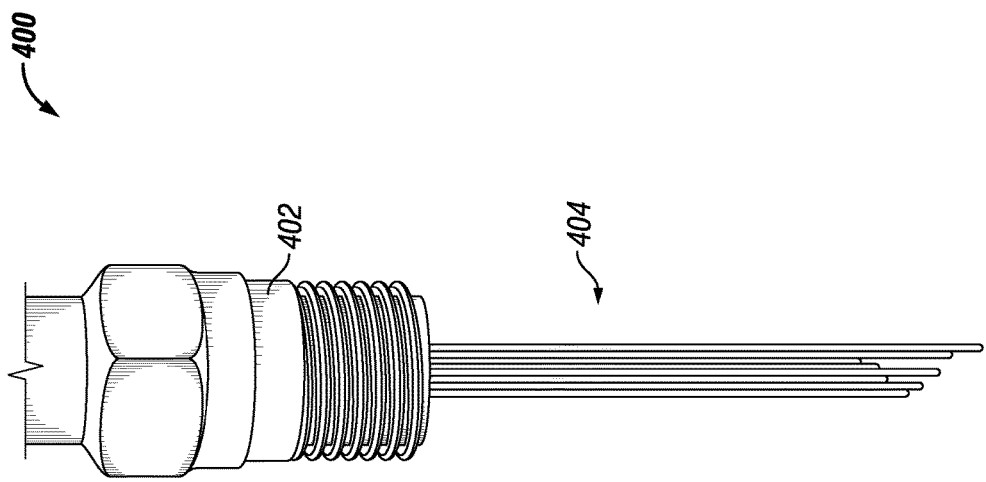

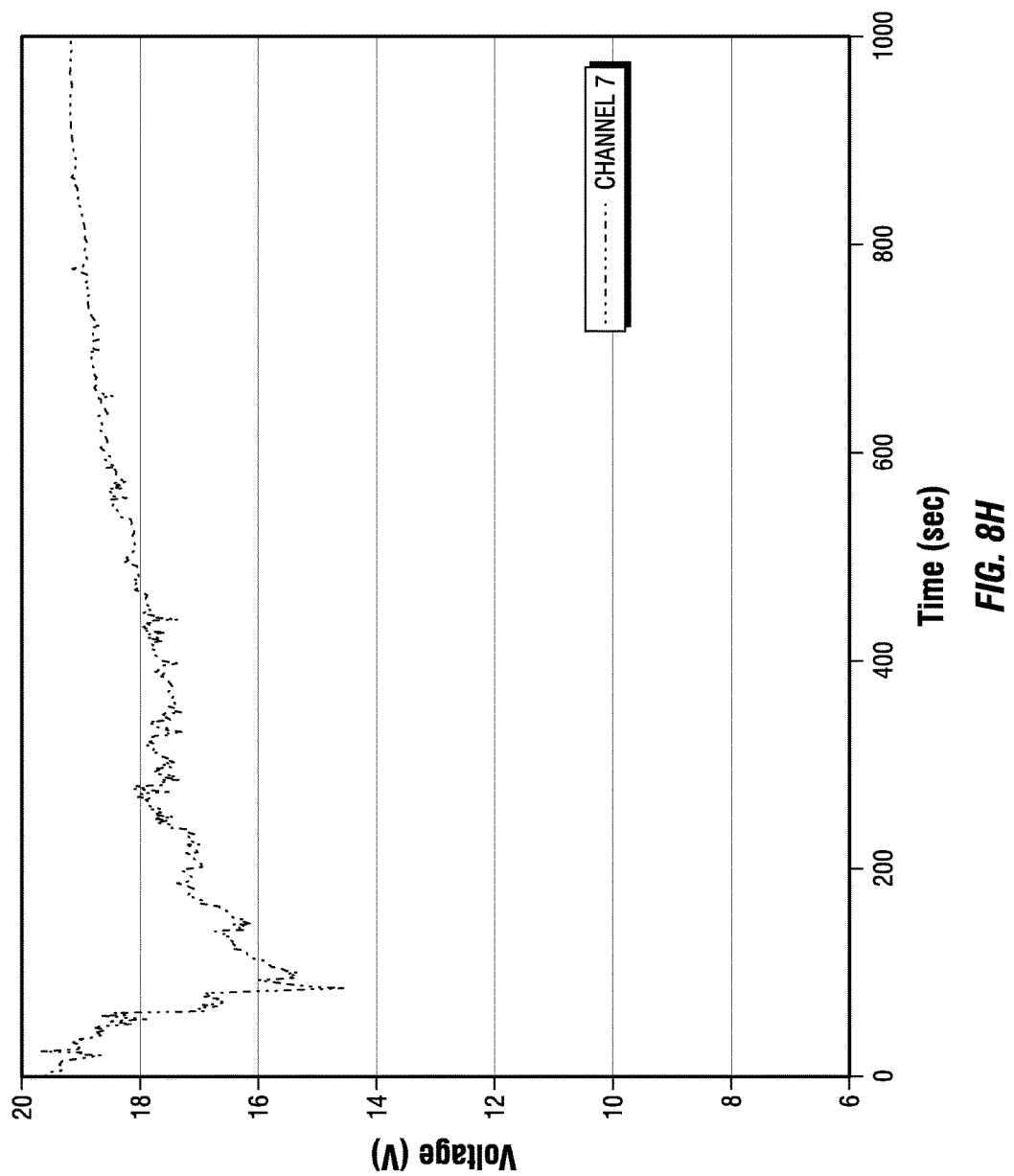

SYSTEM AND METHOD FOR MEASURING SEPARATION RATE OF WATER FROM WATER-IN-CRUDE OIL EMULSIONS

PRIOR RELATED APPLICATIONS

This application claims benefit of U.S. Provisional Patent Application Ser. No. 62/036,301, filed on Aug. 12, 2014.

FEDERALLY SPONSORED RESEARCH STATEMENT

N/A

REFERENCE TO MICROFICHE APPENDIX

N/A

FIELD OF INVENTION

The invention relates to an automated system and method for measuring oil/water separation rate, and, in particular, to a system and method for measuring separation rate of water from water-in-crude oil emulsions at elevated temperatures and/or pressures.

BACKGROUND OF THE INVENTION

Measurement of the separation rate of water from water-in-crude oil emulsions is critical for evaluating performance of a chemical demulsifier used for desalting and dehydration of crude oils in the refining industry. For successful operation of desalting and dehydration processes in a refinery, the best demulsifier chemical must be chosen from a pool of candidate chemicals, often from different supplier companies. Evaluation of demusifiers is further complicated due to relatively low experimental conditions (i.e., below about 195° F. (90° C.)) of most laboratory methods compared to the much higher operating conditions (i.e., about 230° F. (110° C.) to about 300° F. (149° C.)) of most commercial desalters and dehydrators. Therefore, real-world performance of candidate demulsifiers cannot be reliably predicted based on laboratory results at experimental conditions (i.e., below about 195° F.) and must be determined through expensive field trials at commercial operating conditions (i.e., about 230° F. to about 300° F.).

The industry standard for laboratory evaluation of demulsifiers is commonly referred to as a "bottle test." The bottle test (and its variants) involves monitoring the amounts of water separated from a chemically treated emulsion as a function of time. Such measurements are made in glass bottles/tubes with volumetric markings. The separated water settles at the bottom of the glass bottle/tube and forms an interface with the emulsion on top. The amount of water that has separated is estimated periodically by visual inspection of the interface against the volumetric marks. The demulsifier that causes the fastest water separation at experimental conditions (i.e., below about 195° F.) is assumed to be a good candidate for an expensive field trial at operating conditions (i.e., about 230° F. to about 300° F.), which is much higher than the experimental conditions (i.e., below about 195° F.). The bottle test has at least three disadvantages: 1) it cannot be performed safely at temperatures above about 195° F. due to resulting high pressures, 2) it requires determination of real-world performance of candidate demulsifiers through expensive field trials at commercial operating conditions (i.e., about 230° F. to about 300° F.), and 3) it cannot be automated.

In another laboratory method, a single immersed capacitance/conductance probe is used to measure emulsion stability by measuring the amount of water that has separated from oil indirectly.[1] Basically, a water layer is carefully laid down at the bottom of a vessel and an emulsion is carefully spread on top of the bottom water layer. The probe level is set so that conductance is measured in the bottom water layer. As water separates, the separated water becomes part of the bottom water layer. If the salt content of the emulsified water is different than salt content of the initial water, then the electrical properties of the bottom water layer change as the water separates from the emulsion and such change in conductivity is measured by the probe. This method has at least three disadvantages: 1) it is extremely difficult to spread the emulsion on top of the bottom water layer, 2) because it is also limited to lower experimental temperatures, it requires expensive field trials at commercial operating conditions, and 3) it cannot be automated to introduce emulsions.

Another laboratory test that has been developed cannot be used for water-in-crude oil emulsions. Ring electrodes, on the outside of the vessel, are arranged at different depths and used to measure capacitance/conductance of an oil-in-water emulsion.[2] Although the principals of this test may initially seem similar to the present invention, as discussed below, there are critical, non-obvious differences. First, for the ring electrodes, a non-conductive vessel is required, which means the vessel must be fabricated of glass, ceramic or polymer. None of these materials can be safely adapted for elevated temperatures (i.e., about 230° F. to about 300° F.) and the resulting elevated pressures. Second, the ring electrodes must be sized for a larger vessel to provide the necessary resolution. Third, the method requires the water phase to be continuous and the measured conductivity to be correlated with the oil volume fraction (and, thus, is similar to methods used to measure water-drop size). Similar to the other laboratory methods, this method has at least two disadvantages: 1) because it is also limited to lower experimental temperatures, it requires expensive field trials at commercial operating conditions, and 2) it cannot be automated to introduce emulsions at temperatures above the boiling point of water (i.e., above about 212° F. (100° C.)).

Other industrially-used methods are not suitable for the laboratory setting. For example, radar is used industrially to measure separation rate by measuring the interface location; however, its high cost and relative large circular cross-sections makes it difficult (if not impossible) to use in a laboratory setting. Microwave (i.e., Agar probes) and gamma radiation (i.e., Tracerco profiler) are other industrially-used methods that may (or may not) work on a laboratory scale, and, further, they are cost prohibitive for a laboratory setting. A mechanical float would not be robust enough for measuring separation rate of water from water-in-crude oil emulsions in the laboratory.

Therefore, there is a need for an accurate laboratory and/or online system and method for measuring separation rate of water from water-in-crude oil emulsions at elevated temperatures.

SUMMARY OF THE INVENTION

The present invention provides an automated system and method for measuring oil/water separation rates, and, in particular, to a system and method for measuring separation rates of water from water-in-crude oil emulsions at elevated temperatures.

In some embodiments, a system for measuring separation rate in a fluid stream or sample includes an interface (conductivity) cell, an oven or a bath and an analyzer. In an embodiment, the interface cell includes two or more capacitance/conductance probes disposed at different heights from the bottom of the cell. In an embodiment, the oven or bath includes a temperature sensor. The interface cell measures electrolytic conductivity of the fluid stream or sample disposed within the cell at elevated temperatures. The separation rate is determined based on signals received from the interface cell coupled to measure separation rate of the fluid stream or sample.

In particular, the system measures the approximate location of the oil/water interface as a function of time. As the emulsion separates, a continuous water phase forms on the bottom of the interface cell and grows with time. A volume of separated water as function of time can be calculated based on a location of the oil/water interface as a function of time and interface cell dimensions.

For some embodiments, a computer-readable storage-medium contains a program for measuring separation rate in a fluid stream or sample. The program, when executed, performs a method that includes receiving a signal indicative of electrolytic conductivity for the fluid stream or sample from two or more conductance/conductance probes disposed at different heights from the bottom of the interface cell. In addition, the method performed by the program includes determining the separation rate based on the signal and the height of the conductance/conductance probe from the bottom of the interface cell.

The present invention has at least three advantages over current laboratory methods: 1) the present invention can measure separation rate at elevated temperatures and/or pressures, 2) because the present invention can measure separation rate at commercial operating temperatures, it reduces the risk of expensive field trials, and 3) it can be automated. These and other objects, features and advantages will become apparent as reference is made to the following detailed description, preferred embodiments, and examples, given for the purpose of disclosure, and taken in conjunction with the accompanying drawings and appended claims.

BRIEF DESCRIPTION OF THE DRAWINGS

For a further understanding of the nature and objects of the present invention, reference should be made to the following detailed disclosure, taken in conjunction with the accompanying drawings, in which like parts are given like reference numerals, and wherein:

FIG. 2 illustrates a detailed schematic of an interface cell for a separation rate analyzer system according to an embodiment of the present invention;

FIG. 3 illustrates a schematic of a computing device for a separation rate analyzer according to an embodiment of the present invention;

FIG. 4 illustrates a photograph of a prototype interface cell with eight (8) conductivity probes, showing the capacitance/conductance probes mounted at different heights from the bottom of the cell according to an embodiment of the present invention;

FIG. 8H illustrates a chart of time (seconds) versus voltage (V) for channel 7 of a prototype interface cell with eight (8) capacitance/conductance probes for 20% deionized water in low API crude oil emulsion according to an embodiment of the present invention;

DETAILED DESCRIPTION OF EMBODIMENTS OF THE INVENTION

The following detailed description of various embodiments of the present invention references the accompanying drawings, which illustrate specific embodiments in which the invention can be practiced. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. Therefore, the scope of the present invention is defined only by the appended claims, along with the full scope of equivalents to which such claims are entitled.

Figure 1A:
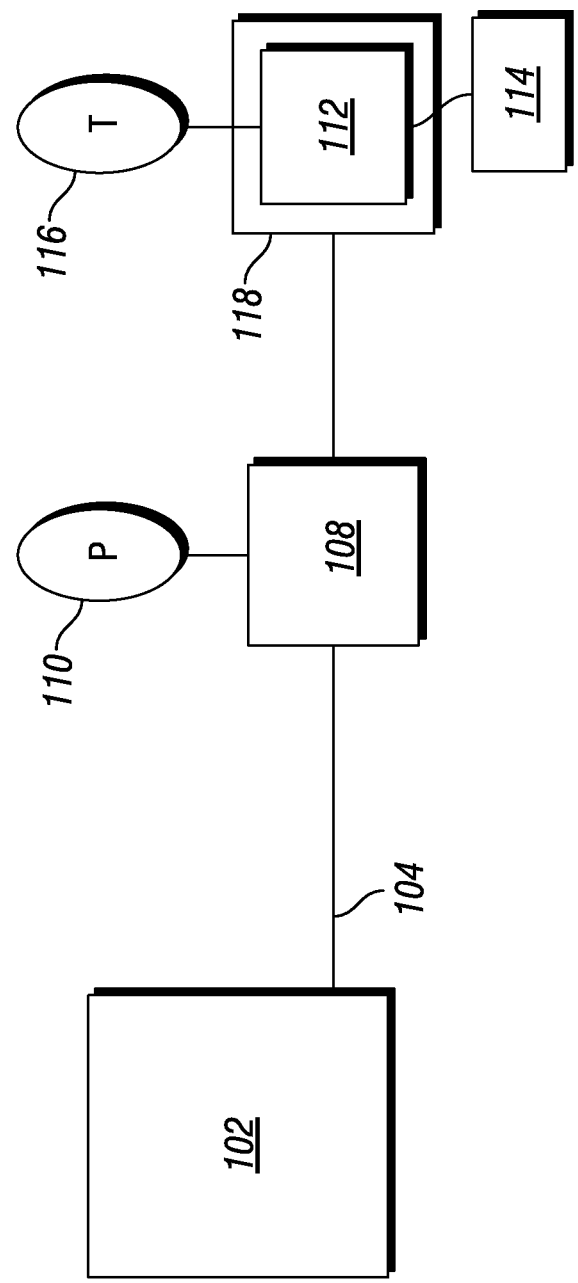
FIG. 1A illustrates a schematic diagram of an exemplary laboratory separation rate analyzer system according to an embodiment of the present invention.
Figure 1B:
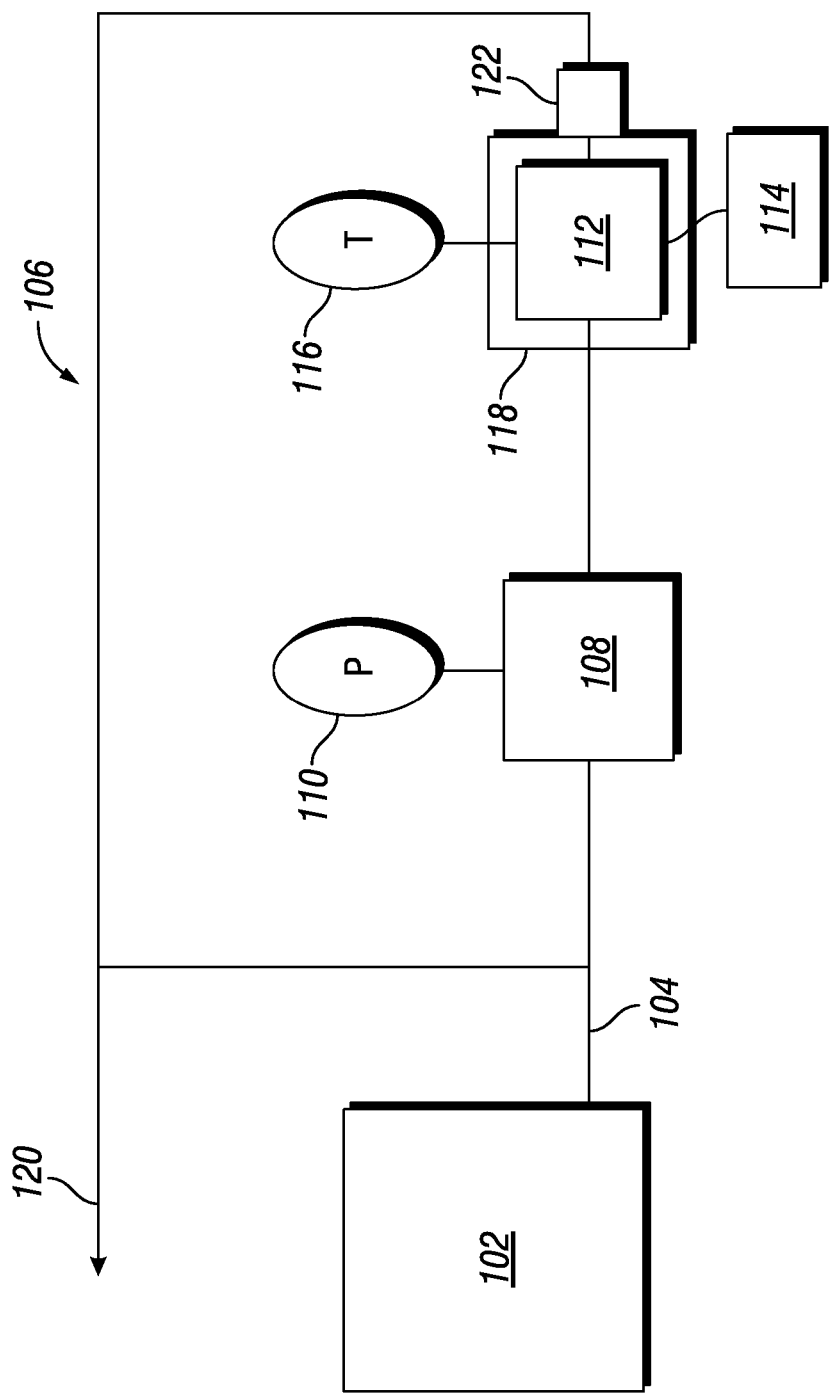
FIG. 1B illustrates a schematic diagram of an exemplary automated laboratory separation rate analyzer system according to an embodiment of the present invention.
Figure 1C:
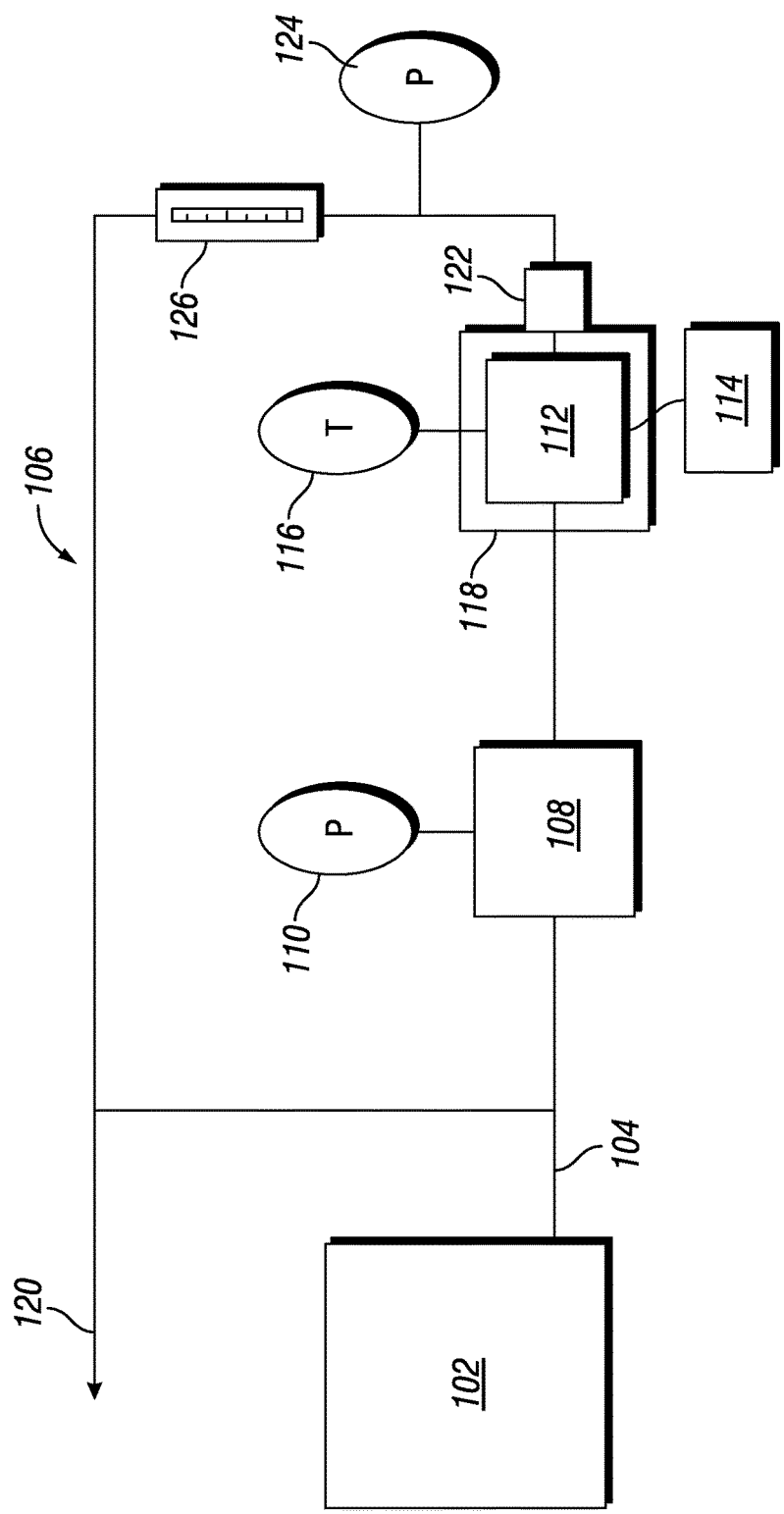
FIG. 1C illustrates a schematic diagram of an exemplary online separation rate analyzer system according to an embodiment of the present invention.

Embodiments of the invention relate to a system and method for measuring separation rate in a fluid stream or sample, such as water from water-in-crude oil emulsions. As illustrated in FIGS. 1A, 1B and 1C, a system 100 includes an interface cell 112, an oven, bath or heater 118 and an analyzer 114.

Although certain sample handling techniques for an exemplary laboratory separation rate analyzer system 100, an exemplary automated laboratory system 100 and an exemplary on-line system 100 are depicted in FIGS. 1A, 1B and 1C and discussed in detail below, a person of ordinary skill in the art (POSITA) could easily combine and adapt these teachings to arrive at other sample handling techniques for the system 100. Accordingly, although certain sample handling techniques are discussed in detail below, this discussion should not be interpreted to exclude other combinations and/or adaptations of these techniques. The use of such sample handling techniques is well known in the art.

In an embodiment, the interface cell 112 includes two or more capacitance/conductance probes 206 disposed at different heights from an inner bottom surface of the interface cell 112. In an embodiment, the interface cell 112 includes a plurality of probes 206 disposed at different heights from the inner bottom surface of the cell 112. In embodiments of the present invention, the number of probes 206 may range from just a few to many. As shown in FIG. 2, six (6) probes 206 may be used in the cell 112; and as shown in FIG. 4, eight (8) probes 206, 404 were used in a prototype interface cell 112, 500. The total number (n) of probes 206 is determined by the desired resolution of the cell 112 and the geometry of the cell 112. The probes may be spaced closer together for better resolution or further apart for less resolution. For example, in a prototype cell 112, 500, the probes 206, 404 were spaced at about 0.1-inch (0.254 cm) apart as shown in FIG. 4.

In an embodiment, the analyzer 114 may be a computer or a computing device as discussed below. In an embodiment, a person may determine a separation rate using a computer based on signals received from two or more capacitance/conductance probes 206 in the interface cell 112 that are coupled to monitor a fluid stream 104. In an embodiment, logic of the analyzer 114 may determine a water separation rate based on signals received from two or more capacitance/conductance probes 206 in the interface cell 112 that are coupled to monitor a fluid stream 104. In an embodiment, the stream 104 is diverted to the cell 112 for analysis. Further, the analyzer 114 may also monitor signals received from an optional temperature sensor 116, an optional pressure sensor 124 and/or an optional flow meter 126.

FIG. 1A illustrates a schematic diagram of an exemplary laboratory system 100 according to an embodiment of the present invention. As shown in FIG. 1A, the system 100 includes an interface cell 112, an oven, bath or heater 118 and an analyzer 114. In an embodiment, the temperature of the oven, bath or heater 118 may be monitored with an optional temperature sensor 116. In an embodiment, the system 100 includes an optional pump 108 and an optional pressure gauge 110. Suitable pumps 108 include low shear pumps including peristaltic pumps to avoid additional, uncontrolled emulsification. In an embodiment, the pump 108 is a peristaltic pump.

In operation of the exemplary laboratory system 100, a source 102 may be an inlet to a crude oil desalter and/or dehydrator in a refinery. In an embodiment, the source 102 may be downstream of a mixer for the desalter and/or dehydrator. At least part of the source 102 enters a fluid stream or sample 104. In an embodiment, the fluid stream or sample 104 may be extracted into a sample vessel or into a sample pipe/tube. If the stream or sample 104 is collected in a sample vessel, the stream or sample 104 should be heated and prepared as an emulsion before transferring the stream or sample 104 in the interface cell 112. In an embodiment, the emulsion of fluid stream or sample 104 may be prepared at the same temperature as the cell 112, and then transferred to the cell 112.

In an embodiment, the emulsion of stream or sample 104 may be prepared at lower temperature and heated to a desired temperature en route to or in the cell 112 before beginning an analysis. For example, the stream or sample 104 may be heated with an oven or bath or heater 118. In an embodiment, the stream or sample 104 may be heated with an in-line heater 118 en route to the cell 112.

If the fluid stream or sample 104 is collected into a sample pipe/tube, the stream or sample 104 may need to be heated to maintain a desired temperature before transferring the stream or sample 104 into the interface cell 112. In an embodiment, the stream or sample 104 may be heated with heat tracing 118 of the sample pipe/tube from the source 102 to the cell 112.

In an embodiment, the fluid stream or sample 104 may be transferred by pouring, piping/tubing and/or pumping the stream or sample 104 into the interface cell 112. In an embodiment, the stream or sample 104 may be manually poured into the cell 112, or, optionally, the stream or sample 104 may be piped/tubed to the cell 112, or, optionally, the stream or sample 104 may be pumped to the cell 112 through pipe/tube that feeds the cell 112. For example, an inlet pipe/tube may be connected at or near the top of the cell 112 and an outlet pipe/tube could be connected at or near the bottom of the cell 112. Such configuration of inlet and outlet would permit the cell 112 to be flushed with stream or sample 104 between analyses.

In an embodiment, the sample piping/tubing may include an optional valve to divert the fluid stream or sample 104 to or around the interface cell 112. In an embodiment, the valves may be manual- or computer-controlled.

Figure 6:
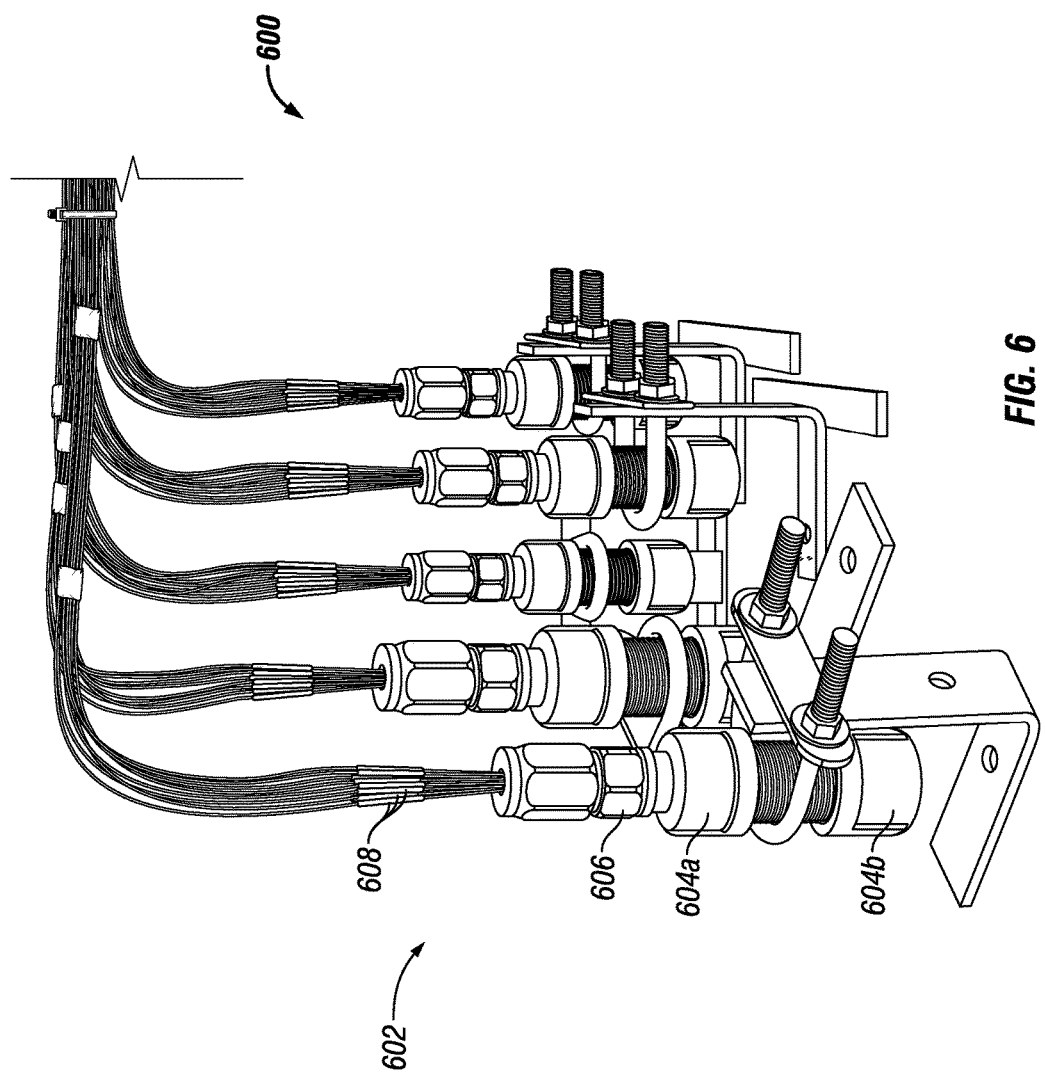
FIG. 6 illustrates a photograph of five (5) assembled prototype cells, showing the interface cell disposed in an oven and connected to a computer according to an embodiment of the present invention.
Figure 10:
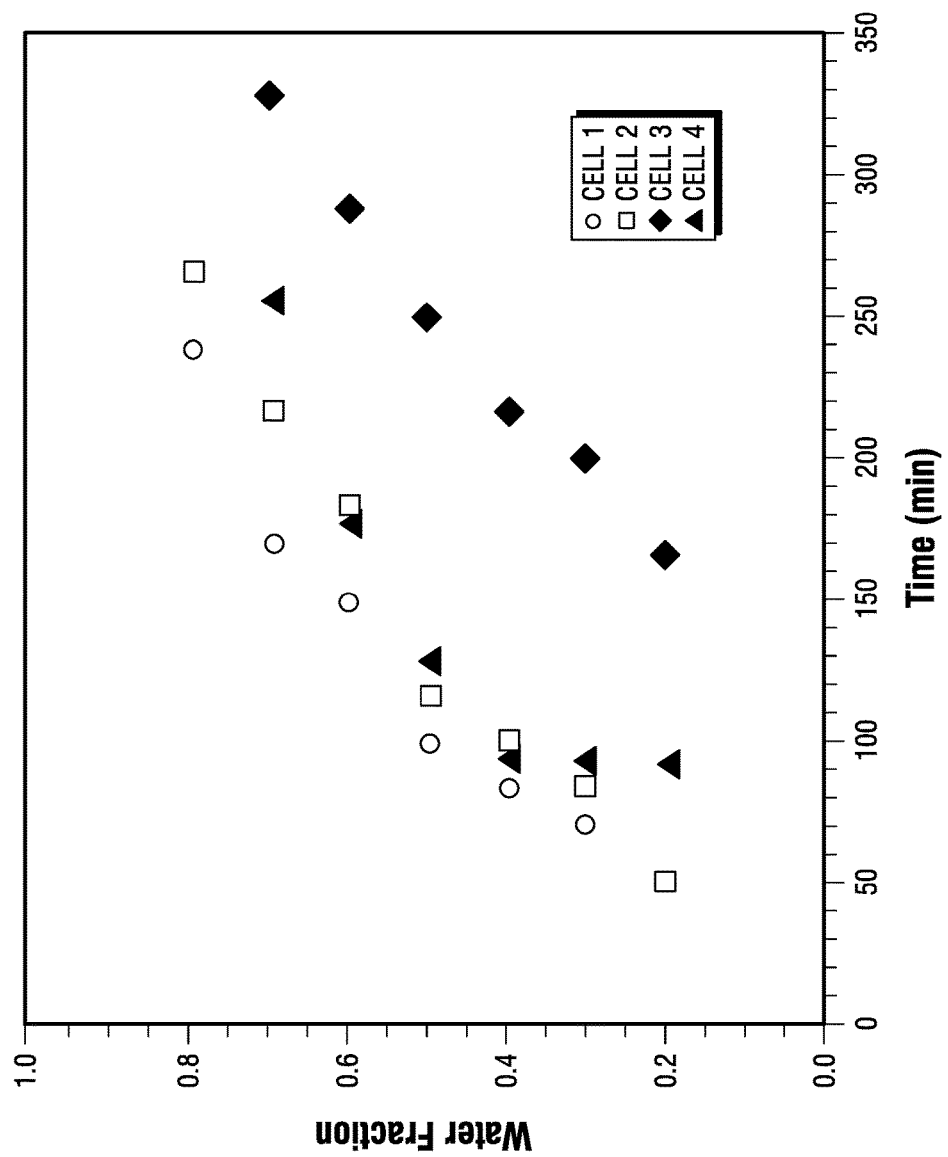
FIG. 10 illustrates a chart of time (seconds) versus water fraction for four (4) prototype interface cells operated in parallel at about 255° F. (i.e., about 125° C.) for a 20% deionized water in heavy API crude oil emulsion according to an embodiment of the present invention.
Figure 12:
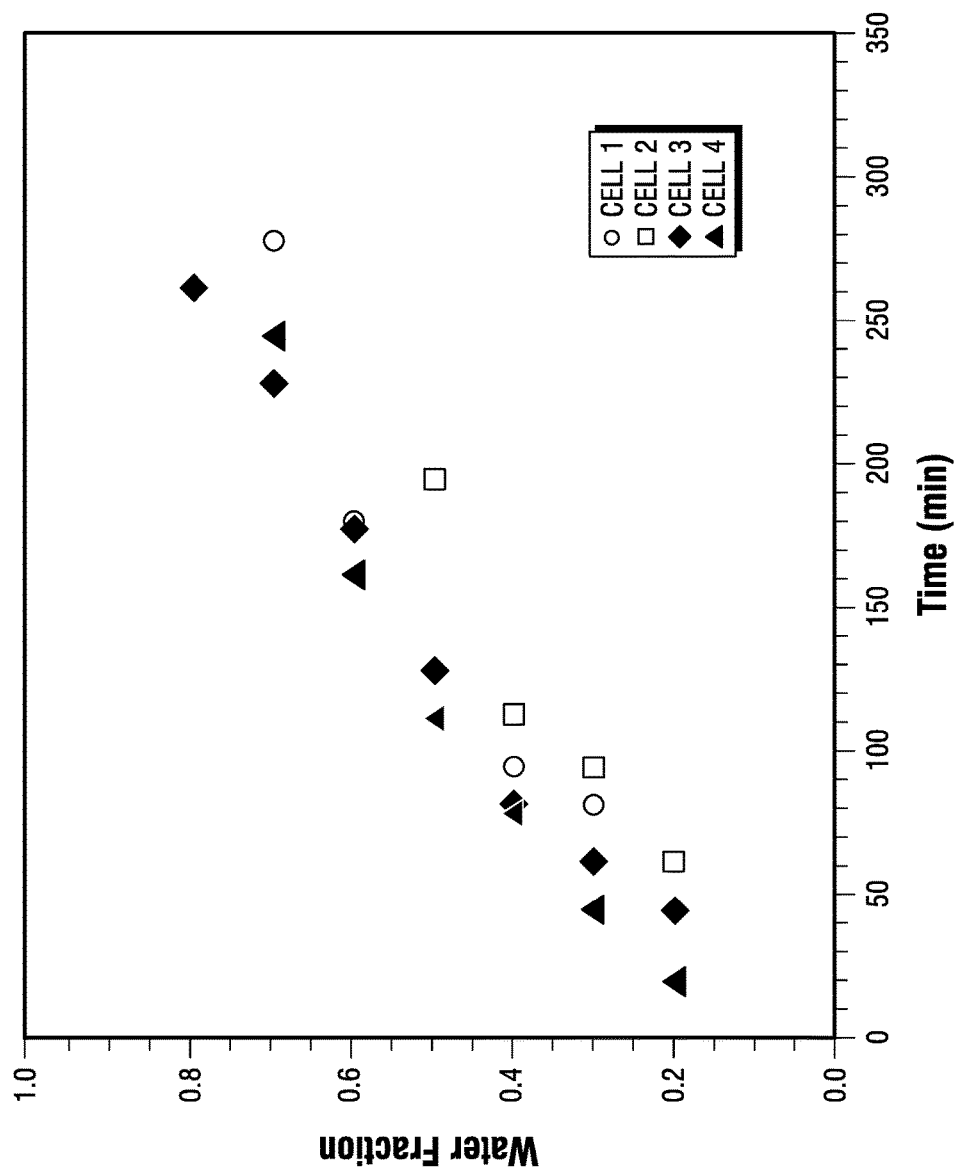
FIG. 12 illustrates a chart of time (minutes) versus water fraction for four (4) prototype interface cells operated in parallel at about 255° F. (i.e., about 125° C.) for 20% deionized water in heavy API crude oil emulsion according to an embodiment of the present invention.

In an embodiment, a plurality of interface cells 112 may be piped/tubed in parallel to allow simultaneous measure of multiple samples. As illustrated in FIG. 6, five (5) prototype interface cells 112, 600 were disposed in an oven 118 in parallel to simultaneously measure multiple samples. As illustrated in FIGS. 10 & 12, four (4) prototype cells 112 were used in parallel to simultaneously collect data from multiple samples.

In an embodiment, the sample piping/tubing may include an optional plurality of valves as part of a manifold to allow simultaneous measurement of multiple samples.

FIG. 1B illustrates a schematic diagram of an exemplary automated laboratory system 100 according to an embodiment of the present invention. As shown in FIG. 1B, the system 100 includes an interface cell 112, an oven, bath or heater 118 and an analyzer 114. In an embodiment, the temperature of the oven, bath or heater 118 may be monitored with an optional temperature sensor 116. If present, the temperature sensor 116 may be disposed within a fluid stream 104 or in an oven, bath or heater 118 disposed around the interface cell 112. Suitable temperature sensors 116 include heat probes, resistance temperature detectors (RTDs), thermocouples, thermometers, and the like.

In an embodiment, the system 100 includes an optional pump 108 and an optional pressure gauge 110. Suitable pumps 108 include low shear pumps including peristaltic pumps to avoid additional, uncontrolled emulsification. In an embodiment, the pump 108 is a peristaltic pump.

In an embodiment, the system includes an optional flow loop 106 and an optional waste outlet 120.

In operation of the exemplary automated laboratory system 100, a source 102 may be an inlet to a crude oil desalter and/or dehydrator in a refinery. In an embodiment, the source 102 may be downstream of a mixer for the desalter and/or dehydrator. At least part of the source 102 enters a fluid stream 104. In an embodiment, the fluid stream 104 may be extracted into a sample pipe/tube. If only a portion of the source 102 is diverted into the flow loop 106, a sufficient pressure differential between entry of fluid stream 104 and exit of the optional flow loop 106 (e.g., optional waste outlet) may ensure flow of the source 102 through the flow loop 106. In an embodiment, the system 100 includes an optional pump 108 and an optional pressure gauge 110 to provide the sufficient pressure differential between entry of the fluid stream 104 and exit of the optional flow loop 106 (e.g., optional waste outlet 120).

In an embodiment, the fluid stream 104 may need to be heated to maintain a desired temperature before transferring the stream 104 into the interface cell 112. In an embodiment, the stream 104 may be heated with heat tracing 118 of the sample/tube from the source 102 to the interface cell 112.

In an embodiment, the stream 104 may be heated to a desired temperature en route to or in the cell 112 before beginning an analysis. For example, the stream 104 may be heated with an oven or bath or heater 118. In an embodiment, the stream 104 may be heated with an in-line heater 118 en route to the cell 112.

In an embodiment, the fluid stream 104 may be transferred by piping/tubing and/or pumping the stream 104 into the interface cell 112. In an embodiment, the fluid stream 104 may be piped/tubed to the cell 112, or, optionally, the stream 104 may be pumped to the cell 112 through a pipe/tube that feeds the cell 112. For example, an inlet pipe/tube may be connected at or near the top of the cell 112 and an outlet pipe/tube could be connected at or near the bottom of the cell 112. Such configuration of inlet and outlet would permit the cell 112 to be flushed with stream 104 between analyses.

In an embodiment, the fluid stream 104 flows to or is pumped to the cell 112 under pressure through a pipe/tube that feeds the cell 112. After the cell 112 is flushed with steam 104, a sample shut off valve 122 would close to stop the flow of the stream 104. After the flow is stopped, the stream 104 in the cell 112 may be allowed to settle for a brief period of time before beginning an analysis. After the analysis is complete, the sample shut-off 122 would open to allow flow of stream 104 to flush the cell 112 again. In an embodiment, the sample shut-off valve 122 may be upstream and/or downstream of the cell 112 as shown in FIG. 3. In an embodiment, the sample shut-off valve 122 may be computer controlled.

In an embodiment, the sample piping/tubing may include an optional valve to divert the fluid stream 104 to or around the interface cell 112. In an embodiment, the valves may be computer-controlled.

In an embodiment, a plurality of interface cells 112 may be piped/tubed in parallel to allow simultaneous measure of multiple samples. As illustrated in FIG. 6, five (5) prototype interface cells 112, 600 were disposed in an oven 118 in parallel to simultaneously measure multiple samples. As illustrated in FIGS. 10 & 12, four (4) prototype cells 112, 500 were used in parallel to simultaneously collect data from multiple samples.

In an embodiment, the sample piping/tubing may include an optional plurality of valves as part of a manifold to allow simultaneous measurement of multiple samples.

FIG. 1C illustrates a schematic diagram of an exemplary online system 100 according to an embodiment of the present invention. As shown in FIG. 1C, the system 100 includes an interface cell 112, an oven, bath or heater 118 and an analyzer 114. In an embodiment, the temperature of the oven, bath or heater 118 may be monitored with an optional temperature sensor 116. If present, the temperature sensor 116 may be disposed within a fluid stream 104 or in an oven, bath or heater 118 disposed around the interface cell 112. Suitable temperature sensors 116 include heat probes, resistance temperature detectors (RTDs), thermocouples, thermometers, and the like.

In an embodiment, the system 100 includes an optional pump 108 and an optional pressure gauge 110. Suitable pumps 108 include low shear pumps including peristaltic pumps to avoid additional, uncontrolled emulsification. In an embodiment, the pump 108 is a peristaltic pump.

In an embodiment, the system 100 includes an optional flow loop 106 and an optional waste outlet 120.

In an embodiment, the system 100 includes an optional pressure gauge 124 and an optional flow meter 126. If present, the optional pressure sensor 124 may be disposed within the fluid stream 104.

In operation of the exemplary on-line system 100, a source 102 may be an inlet to a crude oil desalter and/or dehydrator in a refinery. In an embodiment, the source 102 may be downstream of a mixer for the desalter and/or dehydrator. At least part of the source 102 enters a fluid stream 104. In an embodiment, the stream 104 may be extracted into a sample pipe/tube. If only a portion of the source 102 is diverted into the flow loop 106, a sufficient pressure differential between entry of fluid stream 104 and exit of the optional flow loop 106 (e.g., optional waste outlet) may ensure flow of the source 102 through the flow loop 106. In an embodiment, the system 100 includes an optional pump 108 and an optional pressure gauge 110 to provide the sufficient pressure differential between entry of the fluid stream 104 and exit of the optional flow loop 106 (e.g., optional waste outlet 120). In an embodiment, the interface cell 112, an oven, bath or heater 118, and an optional temperature sensor 116 are disposed along a crude oil desalter and/or dehydrator of a refinery such that the fluid stream 104 contains at least part of the water-in-crude oil emulsion of source 102.

In an embodiment, the fluid stream 104 may need to be heated to maintain a desired temperature before transferring the stream 104 into the interface cell 112. In an embodiment, the stream 104 may be heated with heat tracing 118 of the sample/tube from the source 102 to the cell 112.

In an embodiment, the stream 104 may be heated to a desired temperature en route to or in the cell 112 before beginning an analysis. For example, the stream 104 may be heated with an oven, bath or heater 118. In an embodiment, the stream 104 may be heated with an in-line heater 118 en route to the cell 112.

In an embodiment, the fluid stream 104 may be transferred by piping/tubing and/or pumping the stream 104 into the interface cell 112. In an embodiment, the fluid stream 104 may be piped/tubed to the cell 112, or, optionally, the stream 104 may be pumped to the cell 112 through pipe/tube that feeds the cell 112. For example, an inlet pipe/tube may be connected at or near the top of the cell 112 and an outlet pipe/tube could be connected at or near the bottom of the cell 112. Such configuration of inlet and outlet would permit the cell 112 to be flushed with stream 104 between analyses.

In an embodiment, the fluid stream 104 flows to or is pumped to the cell 112 under pressure through a pipe/tube that feeds the cell 112. After the cell 112 is flushed with steam 104, a sample shut off valve 122 would close to stop the flow of the stream 104. After the flow is stopped, the stream 104 in the cell 112 may be allowed to settle for a brief period of time before beginning an analysis. After the analysis is complete, the sample shut-off 122 would open to allow flow of stream 104 to flush the cell 112 again. In an embodiment, the sample shut-off valve 122 may be upstream and/or downstream of the cell 112 as shown in FIG. 3. In an embodiment, the sample shut-off valve 122 may be computer controlled.

In an embodiment, the sample piping/tubing may include an optional valve to divert the fluid stream 104 to or around the interface cell 112. In an embodiment, the valves may be computer-controlled.

In an embodiment, a plurality of interface cells 112 may be piped/tubed in parallel to allow simultaneous measure of multiple samples. As illustrated in FIG. 6, five (5) prototype cells 112, 600 were disposed in an oven 118 in parallel to simultaneously measure multiple samples. As illustrated in FIGS. 10 & 12, four (4) prototype cells 112, 500 were used in parallel to simultaneously collect data from multiple samples.

In an embodiment, the sample piping/tubing may include an optional plurality of valves as part of a manifold to allow simultaneous measurement of multiple samples.

Interface Cell

As illustrated in FIGS. 1-2 & 4-6, the interface cell 112 represents any device capable of measuring electrolytic conductivity in a fluid stream 104 at different heights from the inner, bottom surface of the cell 112. The cell 112 of the present invention may be cubic-, rectangular-, circular- or circular-like shaped (e.g., elliptical base), and the like. In an embodiment, the interface cell 112 may be a combination of shapes as discussed below.

In an embodiment, an interface cell chamber 202 may be fabricated to have a first base shape and a first height. In an embodiment, a first interface cell cover 204 may be fabricated to have the same base shape as the interface chamber 202 and a second height. In an embodiment, the first base shape may be selected from the group consisting of square, rectangular, circular and ellipse.

In an embodiment, the interface cell chamber 202 includes an interface cell sleeve having a first end and a second end, and a third height. In an embodiment, the first end of the interface cell sleeve may be fabricated to have the same shape as the first interface cell cover 204 and the second end may be fabricated to have a second base shape. In an embodiment, a second interface cell cover may be fabricated to have the same base shape as the second end of the interface cell sleeve and a fourth height. In an embodiment, the second base shape may be selected from the group consisting of square, rectangular, circular and ellipse. In an embodiment, the first base shape may be different than the second base shape.

In an embodiment, the second base shape may be smaller than the first than the base shape such that the sides of the interface cell 112 taper towards the second base shape. The tapered shape has advantages for low-water content emulsions.

Suitable materials for the interface cell chamber 202 and/or cover 204 include any metal compatible with water-in-crude oil emulsions, any plastic compatible with water-in-crude oil emulsions and any combination thereof. In an embodiment, the metal may be selected from the group consisting of carbon steel, stainless steel, stainless steel alloys such as MONEL® (Special Metals Corp.) and HASTALLOY® (Haynes International, Inc.), and the like. In an embodiment, the plastic may be selected from the group consisting of polyether ketone (PEEK), polymethylene (e.g., DELRIN® (DuPont Co.)), polytetrafluorethylene (PTFE) (e.g., TEFLON® (DuPont Co.)) and other high-temperature polymers, and the like. In an embodiment, carbon steel pipe and pipe fittings were used to fabricate a prototype interface cell chamber 202, 502 and cover 204, 504.

Importantly, when an electrically conductive material (e.g., metal) is used for the interface cell chamber 202 and/or cover 204, the two or more capacitance/conductance probes 206 may need to be isolated from the chamber 202 and/or cover 204. In fact, if the chamber 202 is fabricated from an electrically conductive material, the chamber 202 may be used as a required ground for the probes 206; otherwise one of the probes 206 may be used as the ground. Techniques for isolating and sealing the probes 206 in a conductive cover 204 are discussed below.

Although a cylindrical interface chamber 202 and cover 204 are depicted in FIGS. 2 & 4-6, a POSITA could easily adapt these teachings to cubic, rectangular and cylindrical-like interface cell chambers and covers. Accordingly, although the cylindrical interface cell chamber 202 and cover 204 are discussed in detail below, this discussion should not be interpreted to exclude cubic, rectangular and cylindrical-like interface cell chambers and covers.

Although the prototype interface cell chamber 202, 502 and cover 204, 504 were fabricated from pipe and pipe fittings, a POSITA could easily adapt these teachings to other suitable methods of fabricating/machining parts. In an embodiment, the fabrication method may be selected from machining, molding, printing and combinations thereof. For example, if a plastic material is used, the reactor module and cover may be molded by compression or injection molding techniques or printed on a 3-D printer as customary in the art. Accordingly, although machining is discussed in detail below, this discussion should not be interpreted to exclude molding and printing techniques.

An exploded view of an interface cell 200 is depicted in FIG. 2. As shown in FIG. 2, the interface cell chamber 202 has a diameter 208, a height 210 and a thickness 212. The interface chamber 202 may be constructed from a metal or a plastic as discussed above. In an embodiment, the interface cell 200 was constructed from carbon steel.

In an embodiment, the interface cell 200 may have an optional temperature sensor (not shown). When a temperature sensor is used, the interface cell chamber 202 may have an optional temperature probe chamber (not shown) with a temperature probe diameter (not shown) and a temperature probe depth (not shown) extending into the interface cell 200 from an outer surface. Suitable temperature sensors (not shown) include heat probes, resistance temperature detectors (RTDs), thermocouples, thermometers, and the like.

Figure 5:
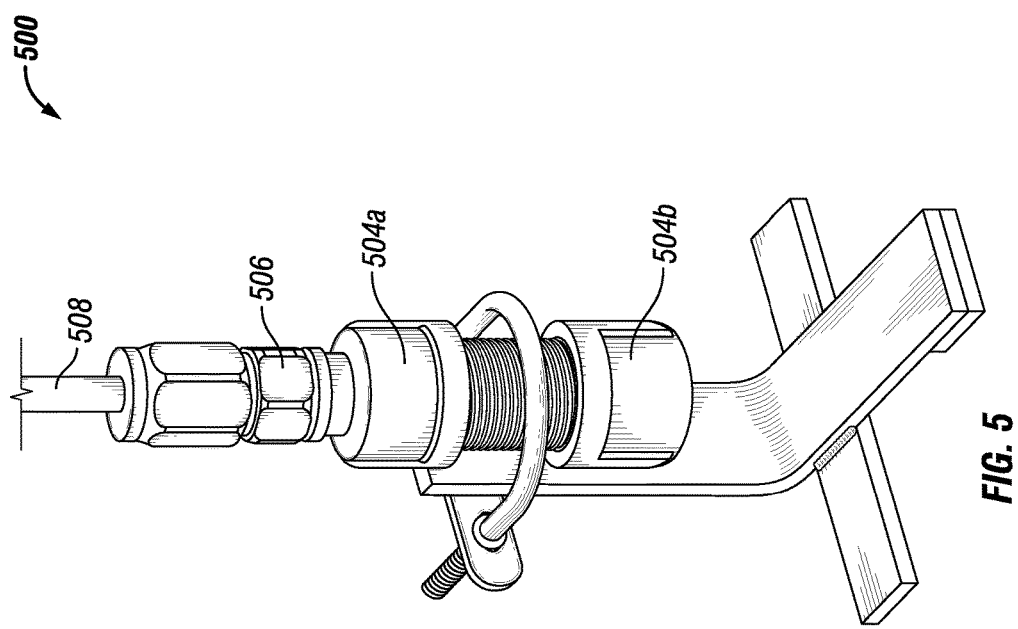
FIG. 5 illustrates a photograph of the assembled prototype interface cell in FIG. 4 showing the probe electrical leads exiting the top of the interface cell according to an embodiment of the present invention.

In an embodiment, the interface cell 200 may have a plurality of holes (not shown) extending into the interface cell chamber 202 material from an upper surface 214 and/or lower surface 216 to attach the first interface cell cover 204. In an embodiment, if the temperature probe chamber extends into the interface cell chamber 202 from an upper surface 214 or lower surface 216, the first interface cell cover 204 will have a temperature probe hole with a temperature probe diameter extending through the first cover 204 and aligning with the temperature probe diameter of the temperature probe chamber in the chamber 202. The first interface cell cover 204 may be constructed from a metal or a plastic as discussed above. In an embodiment, the first interface cell cover 204 was constructed from carbon steel. For example, a prototype interface cell chamber 202, 502 was constructed from a cylindrical carbon steel pipe with a diameter 208 of about 1-inch (2.54 cm), a length 210 of about 3-inches (7.5 cm) and a thickness 212 of about ⅛-inch (0.3 cm) as depicted in FIGS. 4-6.

A plurality of threaded holes (not shown) may be machined into the upper surface 214 and/or a lower surface 216 of the interface cell chamber 202 to receive a plurality of screws. Although screws may be used to secure the first interface cell cover 204 to the interface cell chamber 202, a POSITA could easily adapt this teaching to other fasteners (e.g., compression fitting). In general, any fitting system that provides a leak-free seal between the interface cell chamber 202 and the interface cell cover 204, and maintains the capacitance/conductance probes 206 at a constant height from the inner, bottom surface of the interface cell chamber 202 may be used.

In an embodiment, the interface cell 112, 200 is connected to an inlet and an outlet of fluid stream 104. In an embodiment, a first hole may be machined into the interface cell chamber 202 from an outer surface extending into the chamber 202, and a second hole opposing the first hole may be machined into the chamber 202 from an outer surface extending into the chamber 202. In an embodiment, the first hole may be machined into the interface cell chamber 202 from an outer, upper surface extending into the chamber 202, and the second hole opposing the first hole may be machined into the chamber 202 from an outer, lower surface extending into the chamber 202. In an embodiment, the first hole is fluidically connected to the inlet of fluid stream 104, and the second hole is fluidically connected to the outlet of fluid stream 104. Such configuration of inlet and outlet would permit the cell 112, 200 to be flushed with stream 104 between analyses.

A cylindrical disk may be used to fabricate the first interface cell cover 204. An exploded view of an interface chamber 202 and cover 204 is depicted in FIG. 2. As shown in FIG. 2, the first interface cell cover 204 has a diameter 218, and a height 220. A plurality of holes (not shown) may be machined in the first interface cell cover 204 extending through the cover 204 and aligning with the diameters of the threaded holes in the interface cell chamber 202. For example, a prototype first interface cell cover 204, 504a was constructed from a carbon steel pipe fitting sized to fit a 1-inch (2.54 cm) pipe as depicted in FIGS. 4-6.

Similarly, a cylindrical disk may be used to fabricate the second interface cell cover. The second interface cell cover has a diameter and a height. A plurality of holes may be machined in the second interface cell cover extending through the cover and aligning with the diameters of the threaded holes in the interface cell sleeve. For example, a prototype second interface cell cover 504b was constructed from a carbon steel pipe fitting sized to fit a 1-inch (2.54 cm) pipe as depicted in FIGS. 4-6.

An assembled view of an interface cell chamber 202 and a cover 204 is depicted in FIGS. 4-6. In an embodiment, the interface cell cover 204 was constructed from a pipe fitting.

An assembled view of an interface cell chamber 202 including an interface cell sleeve and a second cover is depicted in FIGS. 4-6. In an embodiment, the interface cell sleeve was constructed from a pipe. In an embodiment, the second interface cell cover was constructed from a pipe fitting.

A temperature probe hole (not shown) may be machined in the first interface cell cover 204 extending through the cover 204 and aligning with the temperature probe diameter of the temperature probe chamber in the interface chamber 202. Suitable temperature probes (not shown) include heat probes, resistance temperature detectors (RTDs), thermocouples, thermometers, and the like.

The first interface cell cover 204 may provide a flange-seal by tightening the cover 204 onto the interface cell chamber 202 via a plurality of screws. In an embodiment, an O-ring may be used between the interface cell chamber 202 and cover 204.

Similarly, the second interface cell cover may provide a flange-seal by tightening the cover onto the interface cell sleeve via a plurality of screws. In an embodiment, an O-ring may be used between the interface cell sleeve and cover.

Alternatively, when the first base shape is circular, the interface cell chamber 202 and first cover 204 may be machined to screw together. For example, when the interface cell chamber 202 was a pipe and pipe fitting, and the cover 204 was a pipe fitting, the cover 204 was screwed onto the interface cell chamber 202.

Similarly, when the second base shape is circular, the interface cell interface sleeve and second cover may be machined to screw together. For example, when the interface cell sleeve was a pipe and the second cover was a pipe fitting, the cover was screwed onto the interface cell sleeve.

As discussed above, the interface cell 112 includes two or more of capacitance/conductance probes 206 disposed at different heights from the inner bottom surface of the interface cell 112. In an embodiment, a plurality of conductance/conductance probes 206 disposed at different heights from the inner bottom surface of the interface cell 112. The number (n) of capacitance/conductance probes may range from just a few to many. As shown in FIG. 2, six (6) capacitance/conductance probes may be used in the interface cell 112; and as shown in FIG. 4, eight (8) capacitance/conductance probes were used in a prototype interface cell 112, 404. The total number of capacitance/conductance probes is determined by the desired resolution of the interface cell 112 and the geometry of the cell 112.

In an embodiment, two or more capacitance/conductance probes 206 may be disposed at different heights from the inner bottom surface of the interface cell 112. In an embodiment, the two or more capacitance/conductance probes 206 may be a welding rod. In an embodiment the capacitance/conductance probes may be any conductive metal. In an embodiment, the conductive metal may be selected from the group consisting of aluminum, copper, nickel, silver, tungsten, zinc, and the like. For example, in the prototype interface cell 112, 500, the capacitance/conductance probes 206, 404 were 1 mm tungsten welding rods for metal inert gas (MIG) welding applications.

One or more holes (not shown) may be machined in the first interface cell cover 204 extending through the cover 204. In an embodiment, the one or more capacitance/conductance probes 206 may be disposed individually through the one or more holes in the first interface cell cover 204 as shown in FIG. 2, or, optionally, as a bundle through the one hole in the first cover 204 as illustrated by FIGS. 4-6. In an embodiment, the individual probes 206 may be secured in place using a metal fitting, a plastic fitting or a combination thereof. In an embodiment, the individual probes 206 may be secured in place using or adhesive. In an embodiment, the plastic may be selected from the group consisting of polytetrafluoroethylene (PTFE) (e.g., TEFLON® (DuPont Co.)) and other high-temperature polymers, and the like. In an embodiment, the adhesive may be selected from the group consisting of epoxy resins, and the like. For example, in the prototype interface cell 112, 500, the capacitance/conductance probes 206, 404 were secured into place using a TEFLON® gland seal fitting 506. After the two or more probes 206 are positioned to a desired height from the inner, bottom surface of the interface cell 112, 500, the gland seal fitting 506 was screwed into an upper prototype cover 504a and tightened to compress an inner TEFLON® seal. In the prototype cell 112, 500, the capacitance/conductance probes 206, 404 were spaced at about 0.1-inch (0.254 cm) apart. As shown in FIG. 4, TEFLON® tape was used on the threads of the gland seal fitting 506.

Although a gland seal may be used to secure the capacitance/conductance probes 206, 404 in place in the interface cell cover 204, 504a, a POSITA could easily adapt this teaching to other fasteners. In general, any fitting system that provides a leak-free seal between the capacitance/conductance probes 206, 404 and the interface cell cover 204, 504a at elevated pressures (e.g., about 100 psig (about 790.8 Kilopascals)), and maintains the capacitance/conductance probes 206, 404 at a constant, known heights from the bottom surface of the interface cell chamber 202 may be used.

The upper cover 504a (assembly) and the lower cover 504b were screwed onto the interface cell chamber 502. As shown in FIG. 5, TEFLON® tape was used on the threads of the interface cell chamber 502.

Computing Device for Separation Rate Analyzer

FIG. 3 illustrates a schematic diagram of a computing device for a separation rate analyzer system according to an embodiment of the present invention. Referring to the drawings in general, and initially to FIGS. 1 and 3 in particular, an exemplary operating environment for implementing embodiments of the present invention is shown and designated generally as a computing device 300 for the analyzer 114. The computing device 300 is but one example of a suitable computing environment and is not intended to suggest any limitation as to the scope of use or functionality of the invention. Neither should the computing device 300 be interpreted as having any dependency or requirement relating to any one or combination of components illustrated.

Embodiments of the invention may be described in the general context of computer code or machine-executable instructions stored as program modules or objects and executable by one or more computing devices, such as a laptop, server, mobile device, tablet, etc. Generally, program modules including routines, programs, objects, components, data structures, etc., refer to code that perform particular tasks or implement particular abstract data types. Embodiments of the invention may be practiced in a variety of system configurations, including handheld devices, consumer electronics, general-purpose computers, more specialty computing devices, and the like. Embodiments of the invention may also be practiced in distributed computing environments where tasks may be performed by remote-processing devices that may be linked through a communications network.

With continued reference to FIG. 3, the computing device 300 of the analyzer 114 includes a bus 310 that directly or indirectly couples the following devices: memory 312, one or more processors 314, one or more presentation components 316, one or more input/output (I/O) ports 318, I/O components 320, a user interface 322 and an illustrative power supply 324. In an embodiment, the two or more capacitance/conductance probes 206 couple directly or indirectly to a signal conditioning device because the probe's raw signal must be processed to provide a suitable signal for an I/O system. The bus 310 represents what may be one or more busses (such as an address bus, data bus, or combination thereof). Although the various blocks of FIG. 3 are shown with lines for the sake of clarity, in reality, delineating various components is not so clear, and metaphorically, the lines would more accurately be fuzzy. For example, one may consider a presentation component such as a display device to be an I/O component. Additionally, many processors have memory. The inventors recognize that such is the nature of the art, and reiterate that the diagram of FIG. 3 is merely illustrative of an exemplary computing device that can be used in connection with one or more embodiments of the present invention. Further, a distinction is not made between such categories as "workstation," "server," "laptop," "mobile device," etc., as all are contemplated within the scope of FIG. 3 and reference to "computing device."

The computing device 300 of the analyzer 114 typically includes a variety of computer-readable media. Computer-readable media can be any available media that can be accessed by the computing device 300 and includes both volatile and nonvolatile media, removable and non-removable media. By way of example, and not limitation, computer-readable media may comprise computer-storage media and communication media. The computer-storage media includes volatile and nonvolatile, removable and non-removable media implemented in any method or technology for storage of information such as computer-readable instructions, data structures, program modules or other data. Computer-storage media includes, but is not limited to, Random Access Memory (RAM), Read Only Memory (ROM), Electronically Erasable Programmable Read Only Memory (EEPROM), flash memory or other memory technology, CD-ROM, digital versatile disks (DVD) or other holographic memory, magnetic cassettes, magnetic tape, magnetic disk storage or other magnetic storage devices, or any other medium that can be used to encode desired information and which can be accessed by the computing device 300.

The memory 312 includes computer-storage media in the form of volatile and/or nonvolatile memory. The memory 312 may be removable, non-removable, or a combination thereof. Suitable hardware devices include solid-state memory, hard drives, optical-disc drives, etc. The computing device 300 of the analyzer 114 includes one or more processors 314 that read data from various entities such as the memory 312 or the I/O components 320.

The presentation component(s) 316 present data indications to a user or other device. In an embodiment, the computing device 300 outputs present data indications including separation rate, temperature, pressure and/or the like to a presentation component 316. Suitable presentation components 316 include a display device, speaker, printing component, vibrating component, and the like.

The user interface 322 allows the user to input/output information to/from the computing device 300. Suitable user interfaces 322 include keyboards, key pads, touch pads, graphical touch screens, and the like. For example, the user may input a type of signal profile into the computing device 300 or output a separation rate to the presentation component 316 such as a display. In some embodiments, the user interface 322 may be combined with the presentation component 316, such as a display and a graphical touch screen. In some embodiments, the user interface 322 may be a portable hand-held device. The use of such devices is well-known in the art.

The one or more I/O ports 318 allow the computing device 300 to be logically coupled to other devices including the interface cell 112, the optional temperature sensor 116, the optional pressure sensor 124, the optional flow meter 126, and other I/O components 320, some of which may be built in. Examples of other I/O components 320 include a printer, scanner, wireless device, and the like.

In operation, a capacitance/conductance probe 206 of the interface cell 112 sends a signal indicative of the electrolytic conductivity to the computing device 300 of analyzer 114 via a first I/O port 318a. Each capacitance/conductance probe 206 must be connected to the first I/O port 318a. For example, if a plurality of probes 206 are used, the first probe 206-1 will be connected to the first I/O port 318a-1, the second probe 206-2 will be connected to the first I/O port 318a-2, etc.

The analyzer 114 includes logic for determining the separation rate of water from water-in-crude oil emulsions based on the signals received from two or more capacitance/conductance probes 206 of the interface cell 112. The stream 104 may consist of, or consist essentially of, water and crude oil in solution.

In some embodiments, the analyzer 114 outputs the separation rate of water from water-in-crude oil emulsions to a presentation component 316 onsite with the interface cell 112 and/or to a remote presentation component 316, such as a display in a control room or offsite monitoring location. The interface cell 112, optionally, temperature sensor 116, optionally, pressure sensor 126 or the analyzer 114 may include a cellular modem or wireless device for this output of the separation rate of water from water-in-crude oil emulsions to the remote location from the interface cell 112. In an embodiment, the presentation component 316 may show present data indications including a separation rate (e.g. water fraction/minute) of the stream 104, optionally, temperature of the stream 104 in degree Fahrenheit (° F.) or in degree Celsius (° C.), and, optionally, pressure of the stream 104 in pounds per square inch gauge (psig) or in kilopascals (KPa).

In an embodiment, the analyzer 114 operates at temperatures between about 150 to 350° F. (i.e., about 65.5 to about 176.7° C.) or an upper limit defined by component temperature ratings. In an embodiment, the analyzer 114 may operate at temperatures higher than about 350° F. Some embodiments include the temperature sensor 116, which can provide assurance that the temperature is in an acceptable range. In these embodiments, the computing device 300 receives a second signal from the pressure sensor 116 via a second I/O port 318b, as discussed above.

The temperature sensor represents any device capable of measuring temperature of the fluid stream 104. The temperature sensor 116 represents any device capable of measuring temperature of the fluid stream 104. Examples of temperature sensors 116 include heat probes, resistance temperature detectors (RTD), thermocouples, thermometers, and the like. The temperature sensor 116 enables determining temperature of the stream 104 when passing through the interface cell 112 and, thus, the temperature sensor 116 may be disposed at or near the interface cell 112.

Some embodiments utilize the temperature sensor 116 located directly in contact with the fluid stream 104. In other words, the temperature sensor 116 may be inserted directly into the stream 104. For other embodiments, the temperature sensor 116 operates as part of a temperature-regulating device such as an oven, bath or heater 118 that controls temperature of the stream 104 such that the stream temperature remains constant when passing through the conductivity cell 112. If the second signal representing temperature of the fluid stream 104 decreases below a first threshold value or increases above a second threshold value, the computing device 300 of analyzer 114 may, thus, indicate an error or otherwise tag the separation rate that is determined and output. In an embodiment, the computing device 300 may initiate a separation rate determination when the second signal reaches a first threshold value.

In an embodiment, the analyzer 114 operates at pressures between about 0 to 100 psig (i.e., about 101.4 to about 790.8 kilopascal) or an upper limit defined by component pressure ratings. Some embodiments include the pressure sensor 110 or 124, which can provide assurance that the pressure is in an acceptable range. The pressure sensor 110, 124 represents any device capable of measuring pressure of the fluid stream 104. In these embodiments, the computing device 300 receives a third signal from the pressure sensor 110 or 124 via a third I/O port 318c, as discussed above. If the third signal representing pressure of fluid stream 104 increases above a threshold value, the computing device 300 of analyzer 114 may, thus, indicate an error or otherwise tag the separation rate that is determined and output.

In some embodiments, a flow meter 126 disposed along the flow loop 106 confirms that the fluid stream 104 is flowing through the interface cell 112 since the fully-automated system 100 can provide real-time online measurements as separation rates are determined. The flow meter 126 represents any device capable of measuring flow rate of the fluid stream 104. The separation rate would fail to be updated over time in the absence of the stream 104 moving through the flow loop 106. If flow stops or slows below a threshold value, the computing device 300 of analyzer 114 may, thus, indicate an error or otherwise tag the separation rate that is determined and output. In these embodiments, the computing device 300 receives a fourth signal from the flow meter 126 via a fourth I/O port 318d.

In some embodiments, the analyzer 114 may output the separation rate at specified intervals, such as every two to eight hours. Continuous automatic monitoring by the analyzer 114 permits integration of the analyzer 114 with other process controls that can adjust levels of the temperature, pressure and/or flow rate in the stream 104 based on the separation rate that is determined. For some embodiments, the analyzer 114 may output an alarm signal if the separation rate falls below a minimum value.

The stream 104 exits the flow loop 106 and is sent as a waste output 120 for treatment or reuse. The waste output 120 may include any of the stream 104 not diverted through the flow loop 106. In some embodiments, at least about 7 psig (i.e., about 50 kilopascal) pressure differential between where part of the stream 104 enters the flow loop 106 and combines back to form the waste output 120 maintains desired flow.

Method of Measuring Separation Rate of Water from Water-in-Crude Oil Emulsions

Figure 7:
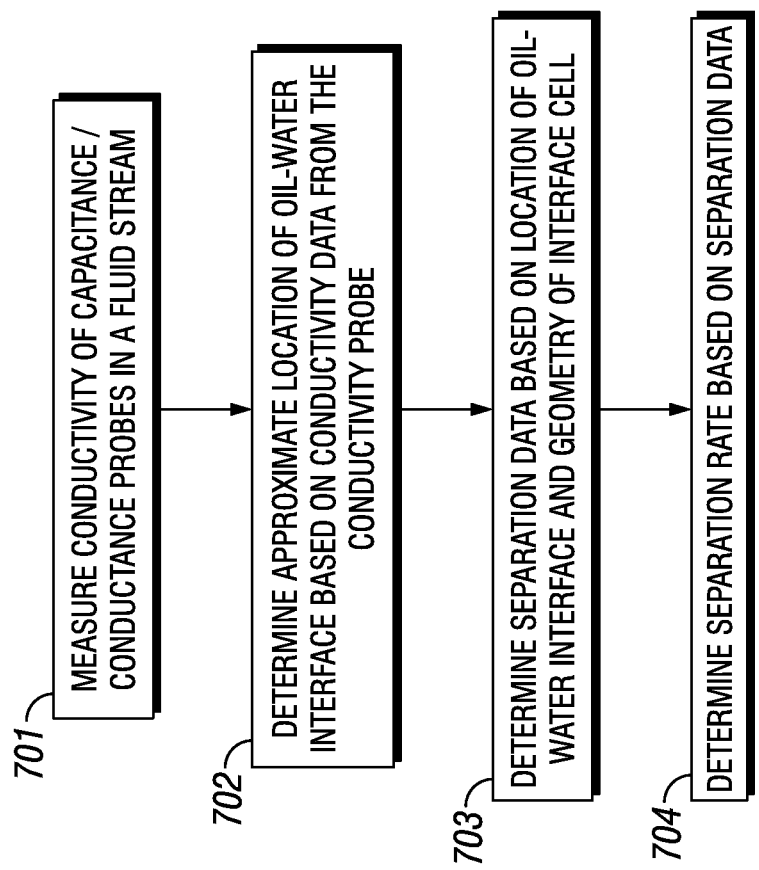
FIG. 7 illustrates a flow chart for a method of measuring separation rate of water from water-in-crude oil emulsion according to an embodiment of the present invention.
Figure 8A:
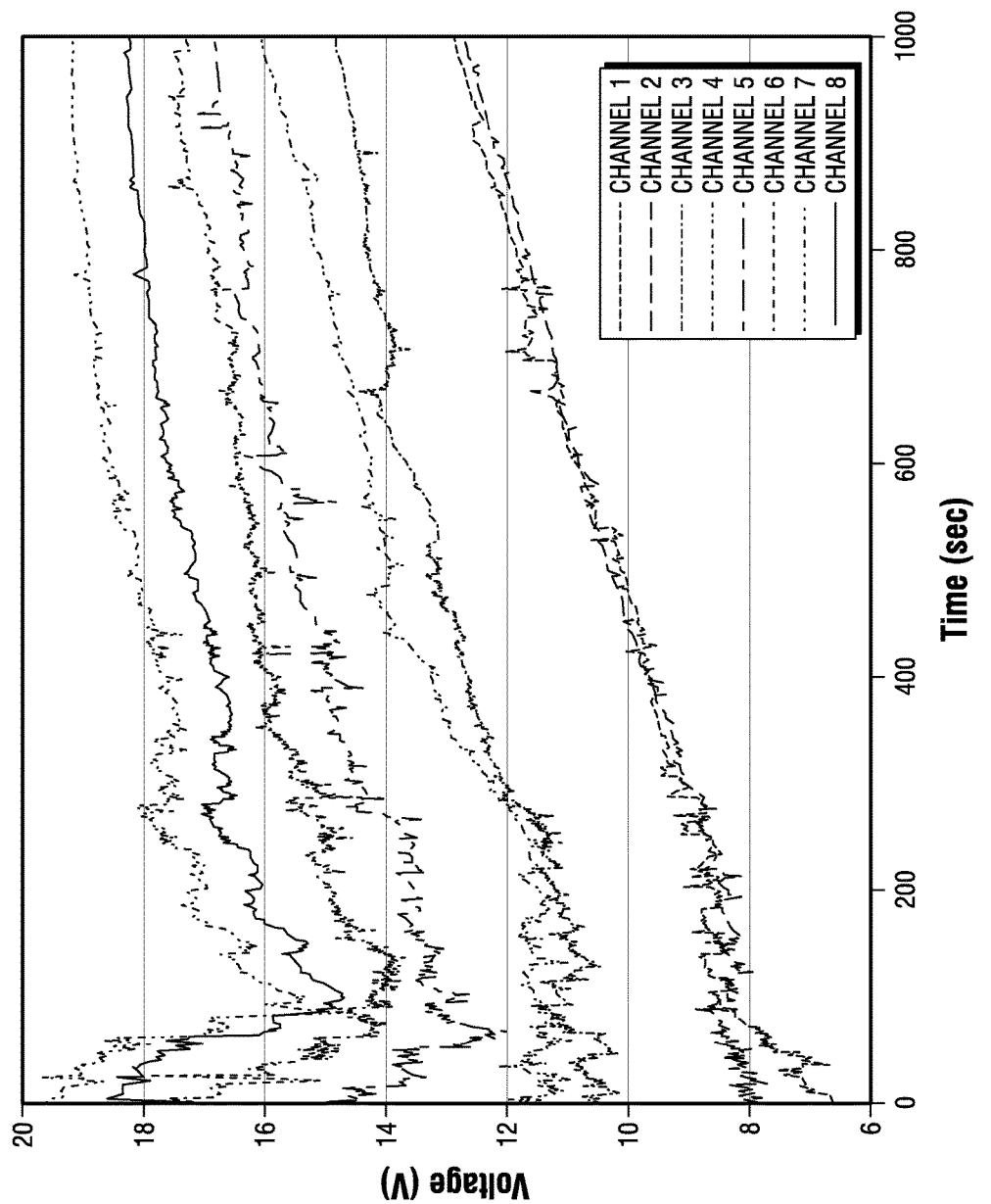
FIG. 8A illustrates a chart of time (seconds) versus voltage (V) for a prototype interface cell with eight (8) capacitance/conductance probes for 20% deionized water in low API crude oil emulsion according to an embodiment of the present invention.
Figure 8B:
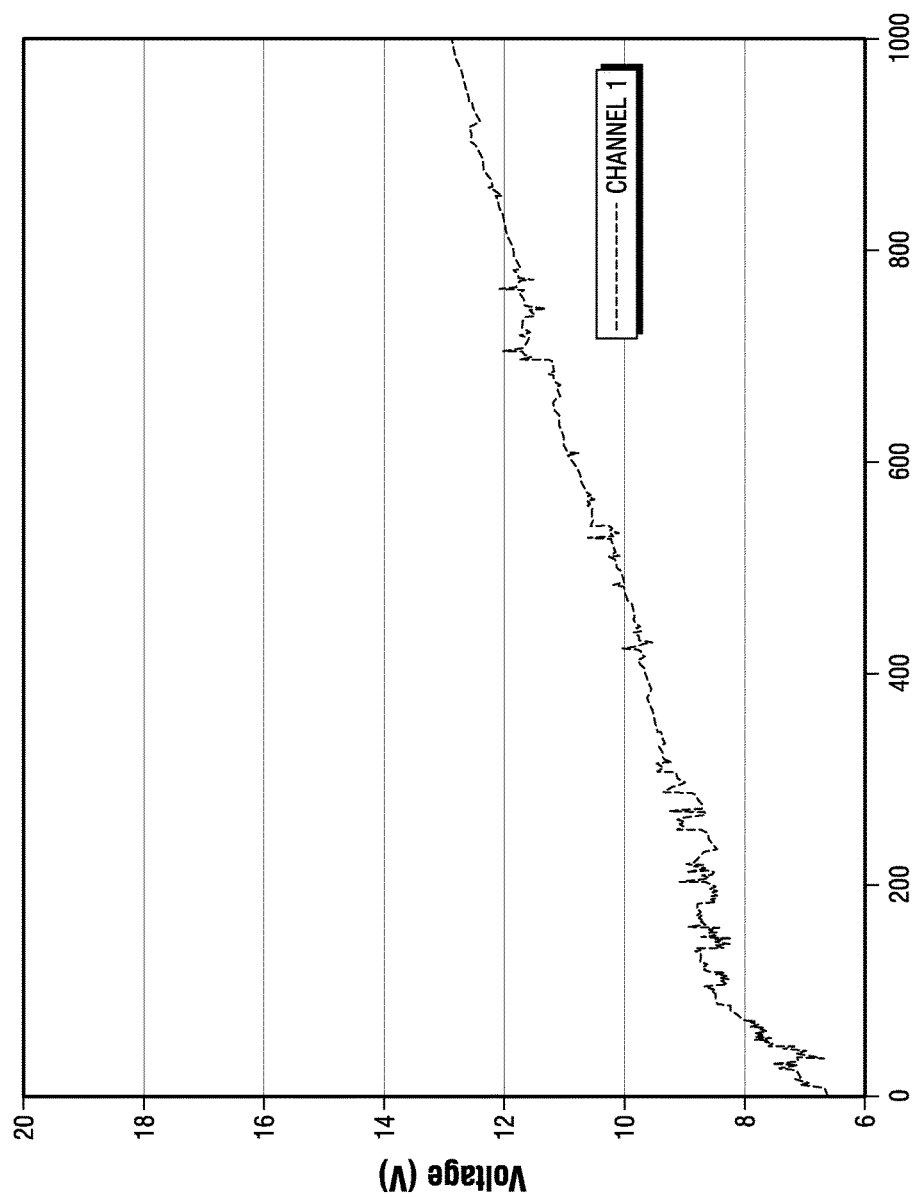
FIG. 8B illustrates a chart of time (seconds) versus voltage (V) for channel 1 of a prototype interface cell with eight (8) capacitance/conductance probes for 20% deionized water in low API crude oil emulsion according to an embodiment of the present invention.
Figure 8C:
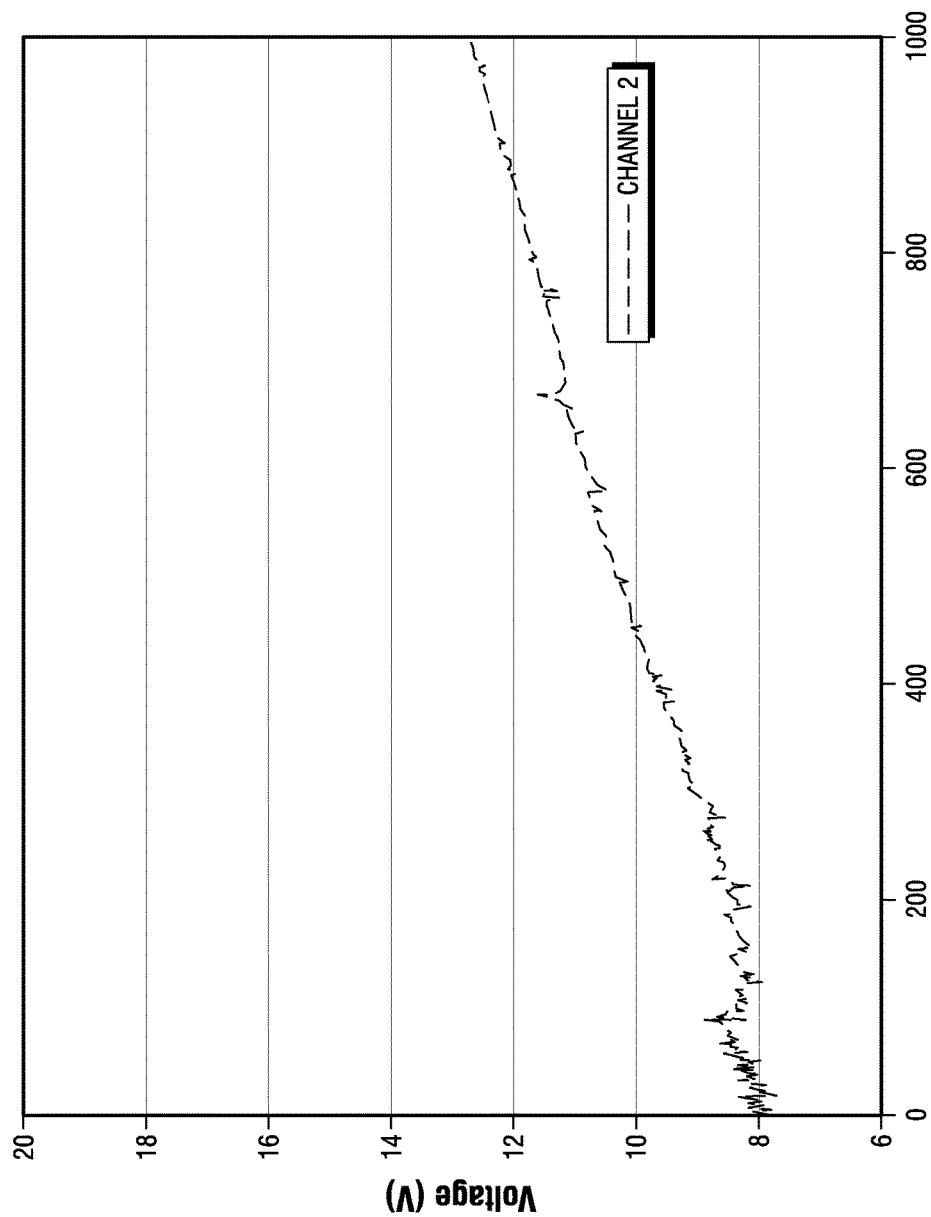
FIG. 8C illustrates a chart of time (seconds) versus voltage (V) for channel 2 of a prototype interface cell with eight (8) capacitance/conductance probes for 20% deionized water in low API crude oil emulsion according to an embodiment of the present invention.
Figure 8D:
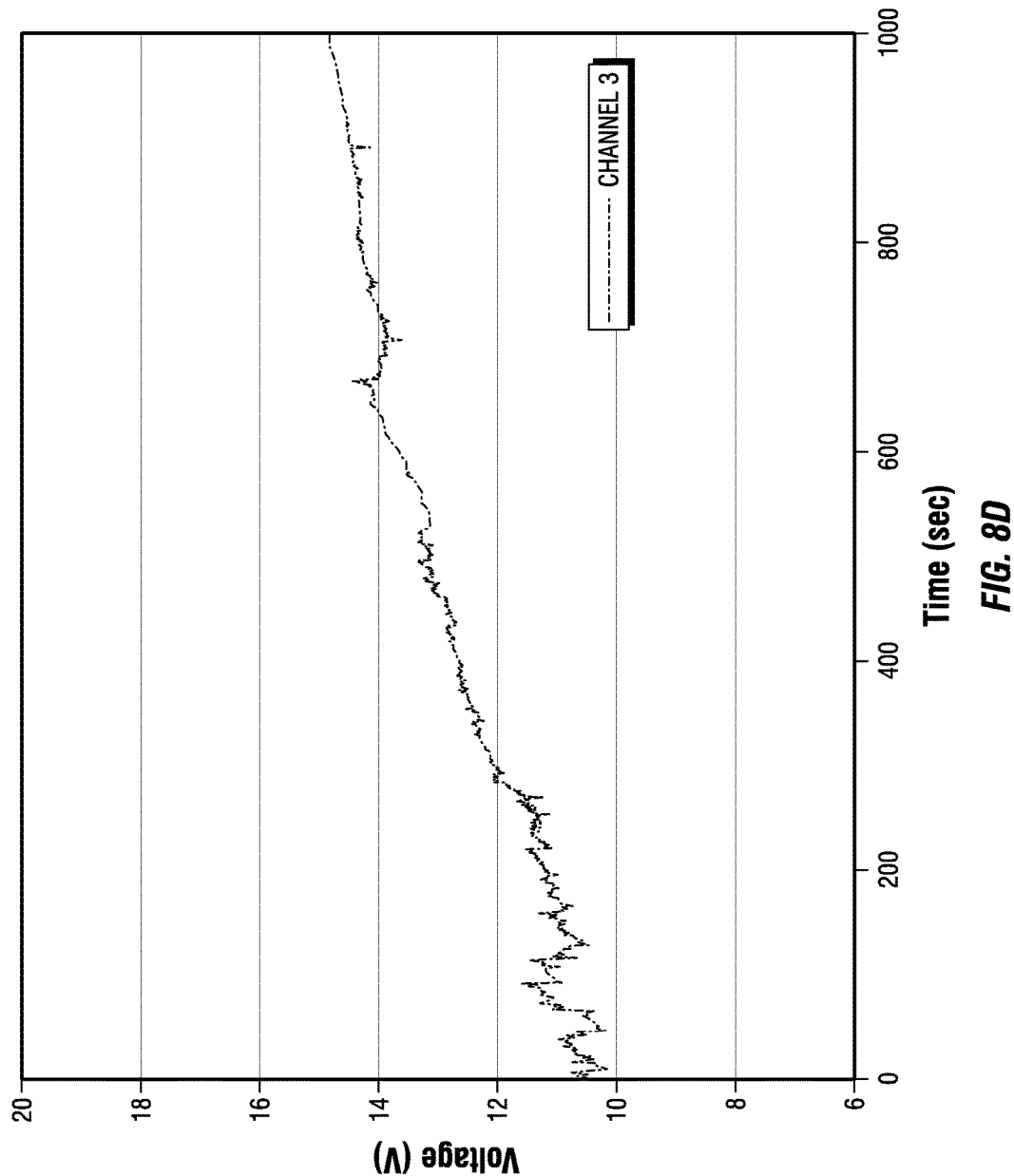
FIG. 8D illustrates a chart of time (seconds) versus voltage (V) for channel 3 of a prototype interface cell with eight (8) capacitance/conductance probes for 20% deionized water in low API crude oil emulsion according to an embodiment of the present invention.
Figure 8E:
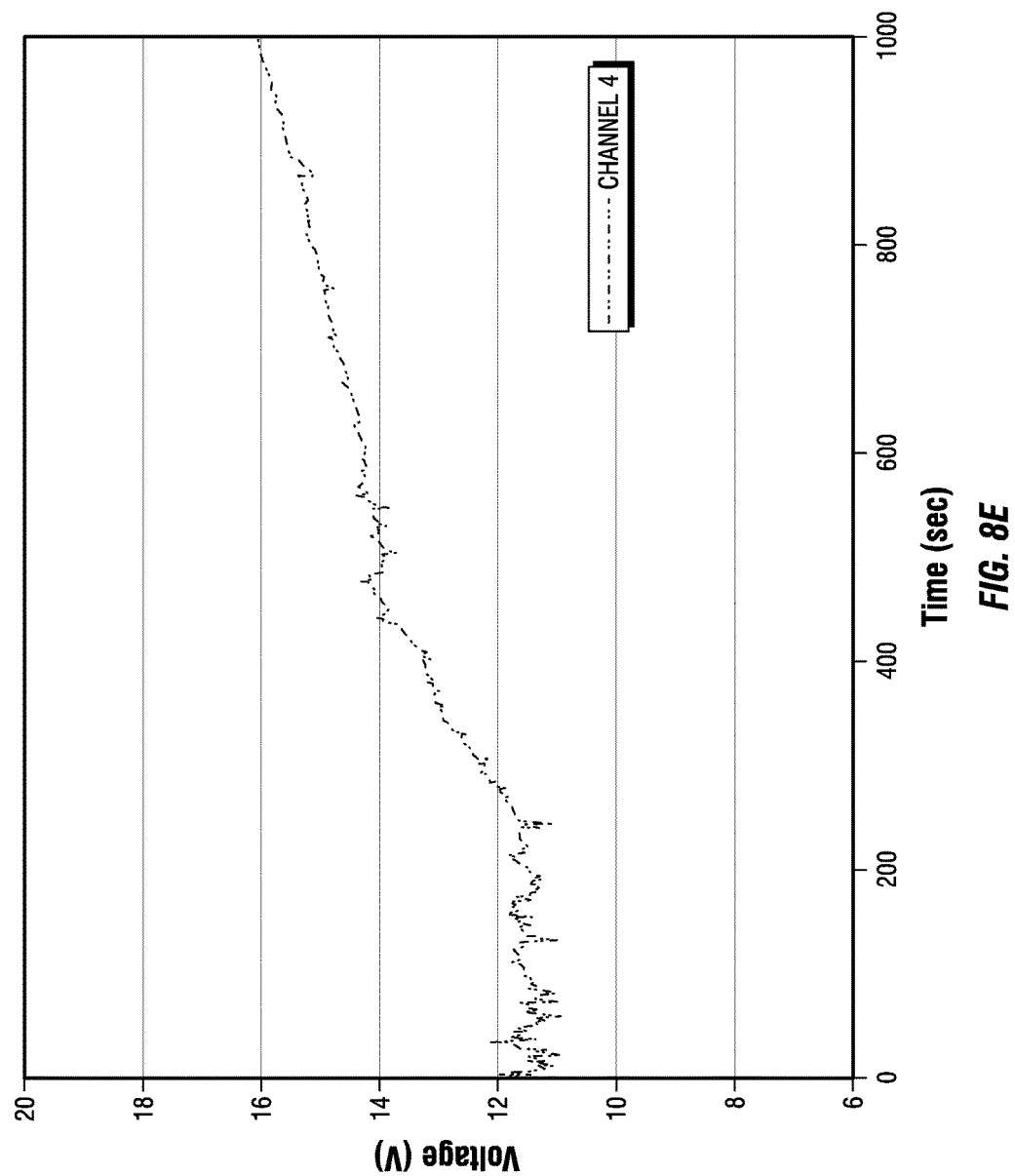
FIG. 8E illustrates a chart of time (seconds) versus voltage (V) for channel 4 of a prototype interface cell with eight (8) capacitance/conductance probes for 20% deionized water in low API crude oil emulsion according to an embodiment of the present invention.
Figure 8F:
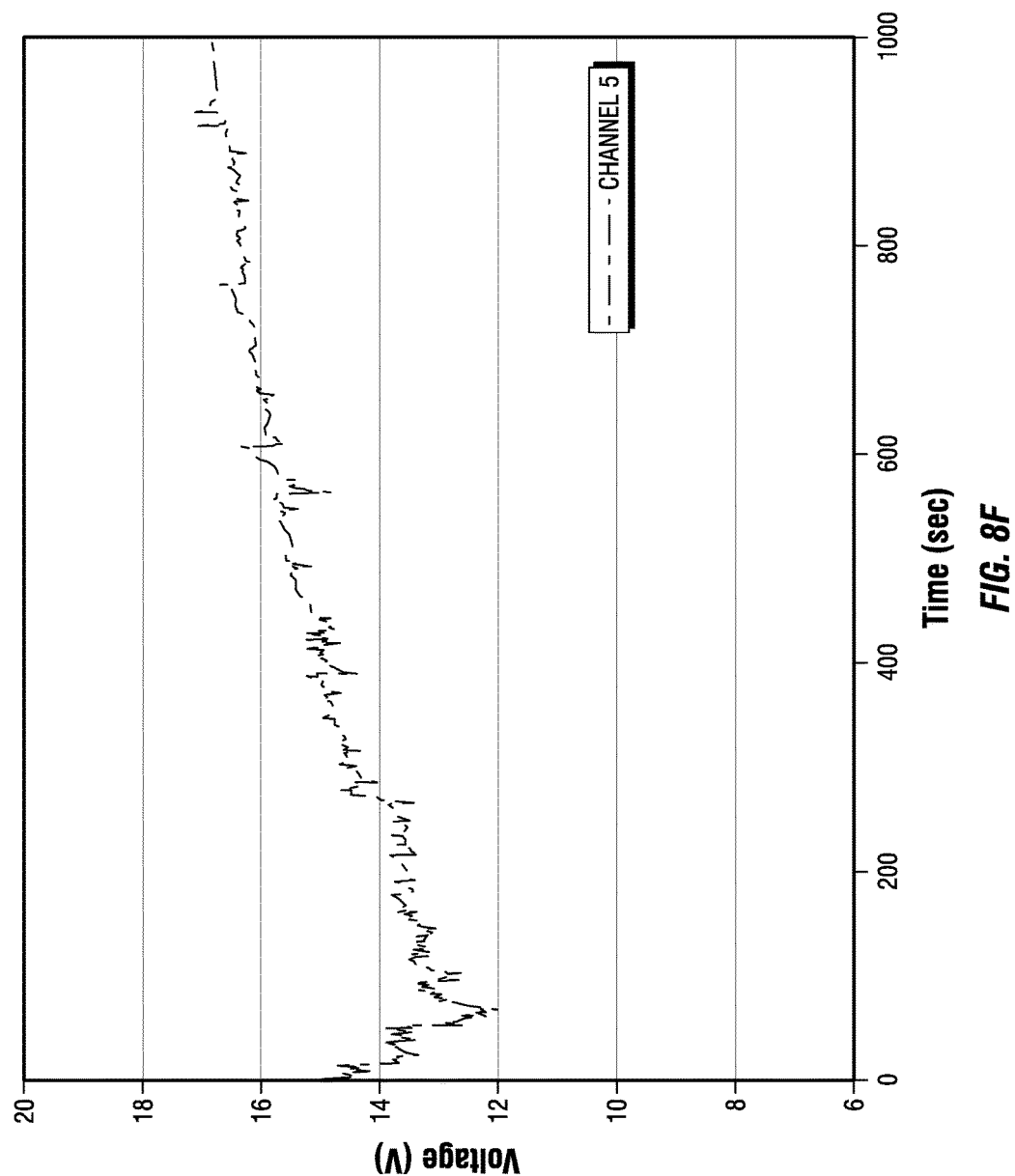
FIG. 8F illustrates a chart of time (seconds) versus voltage (V) for channel 5 of a prototype interface cell with eight (8) capacitance/conductance probes for 20% deionized water in low API crude oil emulsion according to an embodiment of the present invention.
Figure 8G:
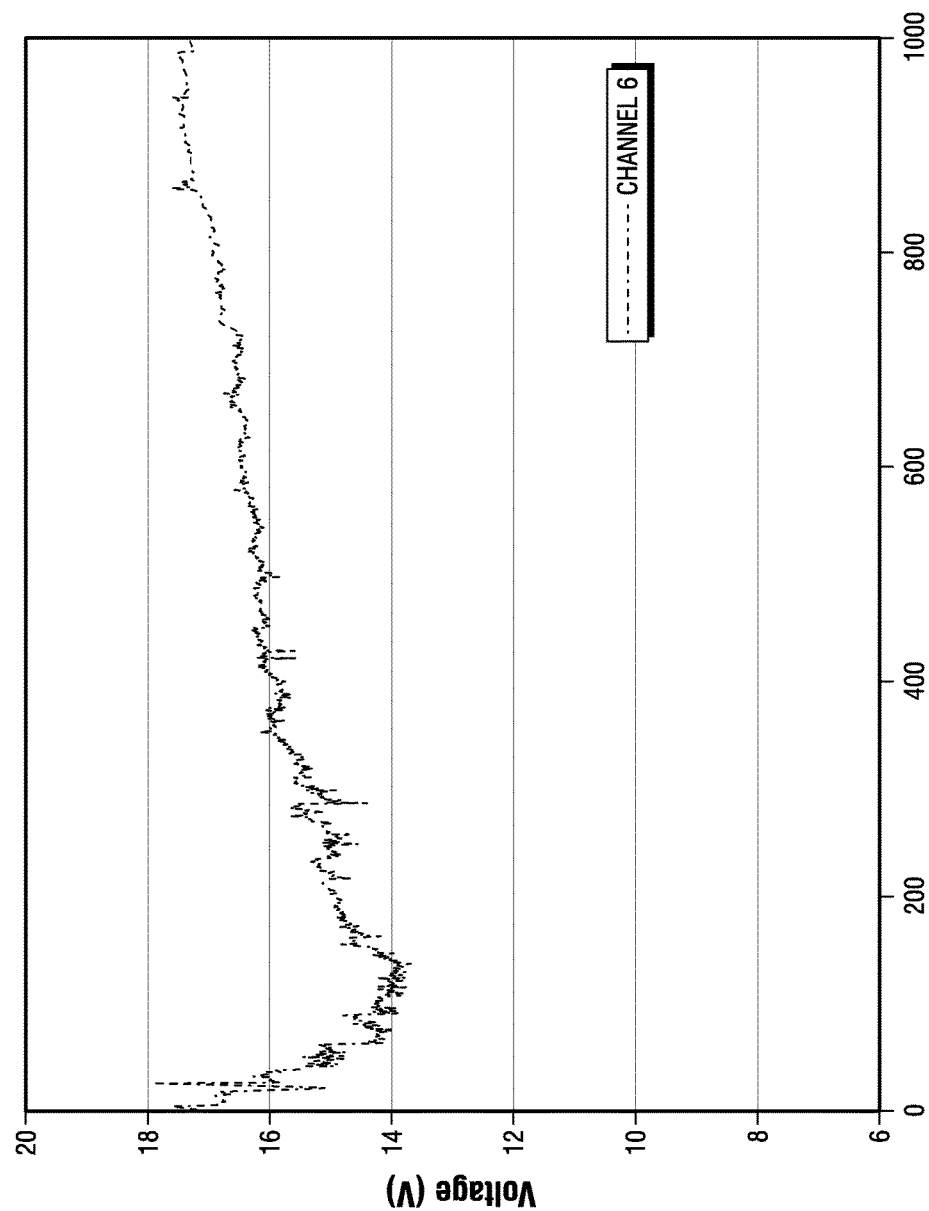
FIG. 8G illustrates a chart of time (seconds) versus voltage (V) for channel 6 of a prototype interface cell with eight (8) capacitance/conductance probes for 20% deionized water in low API crude oil emulsion according to an embodiment of the present invention.
Figure 8I:
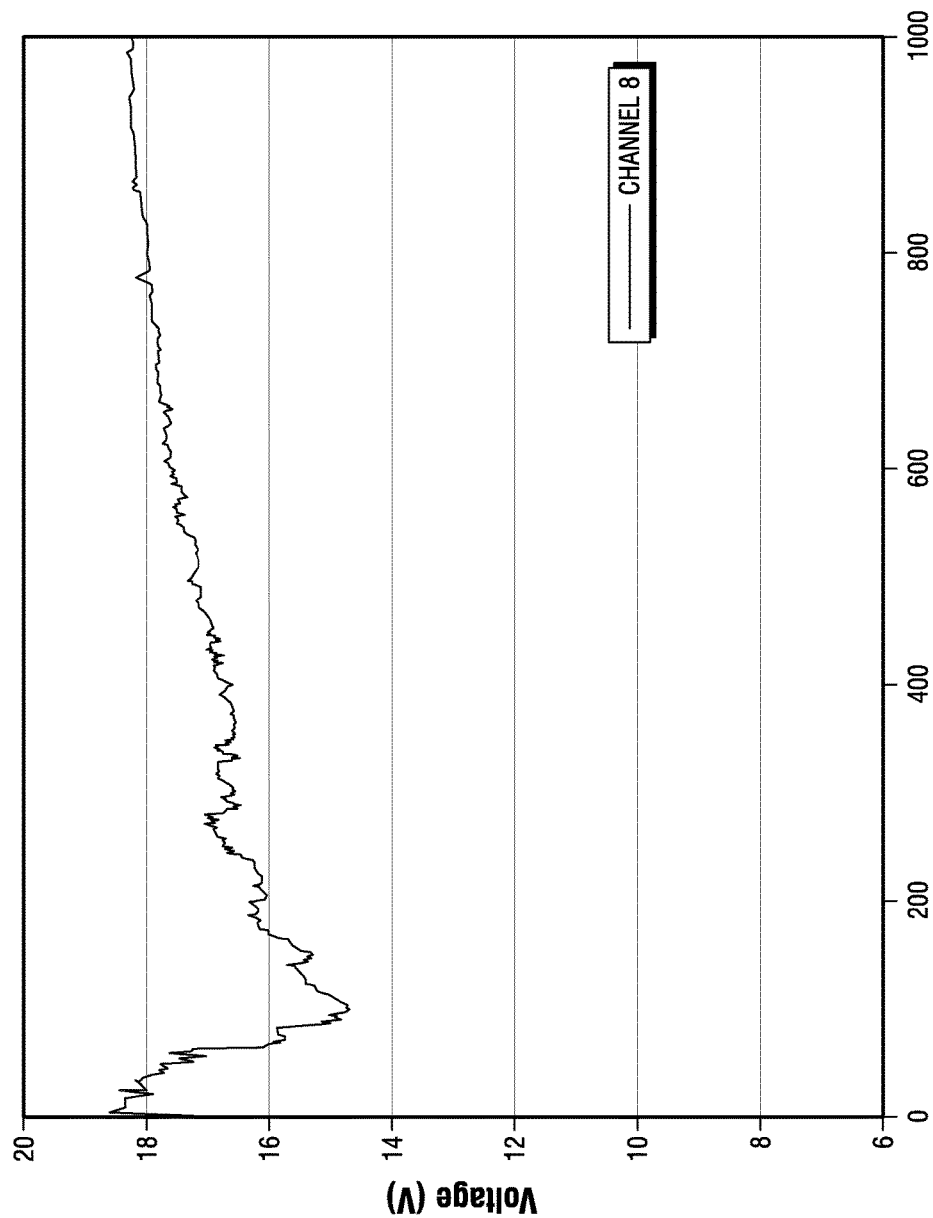
FIG. 8I illustrates a chart of time (seconds) versus voltage (V) for channel 8 of a prototype interface cell with eight (8) capacitance/conductance probes for 20% deionized water in low API crude oil emulsion according to an embodiment of the present invention.
Figure 9A:
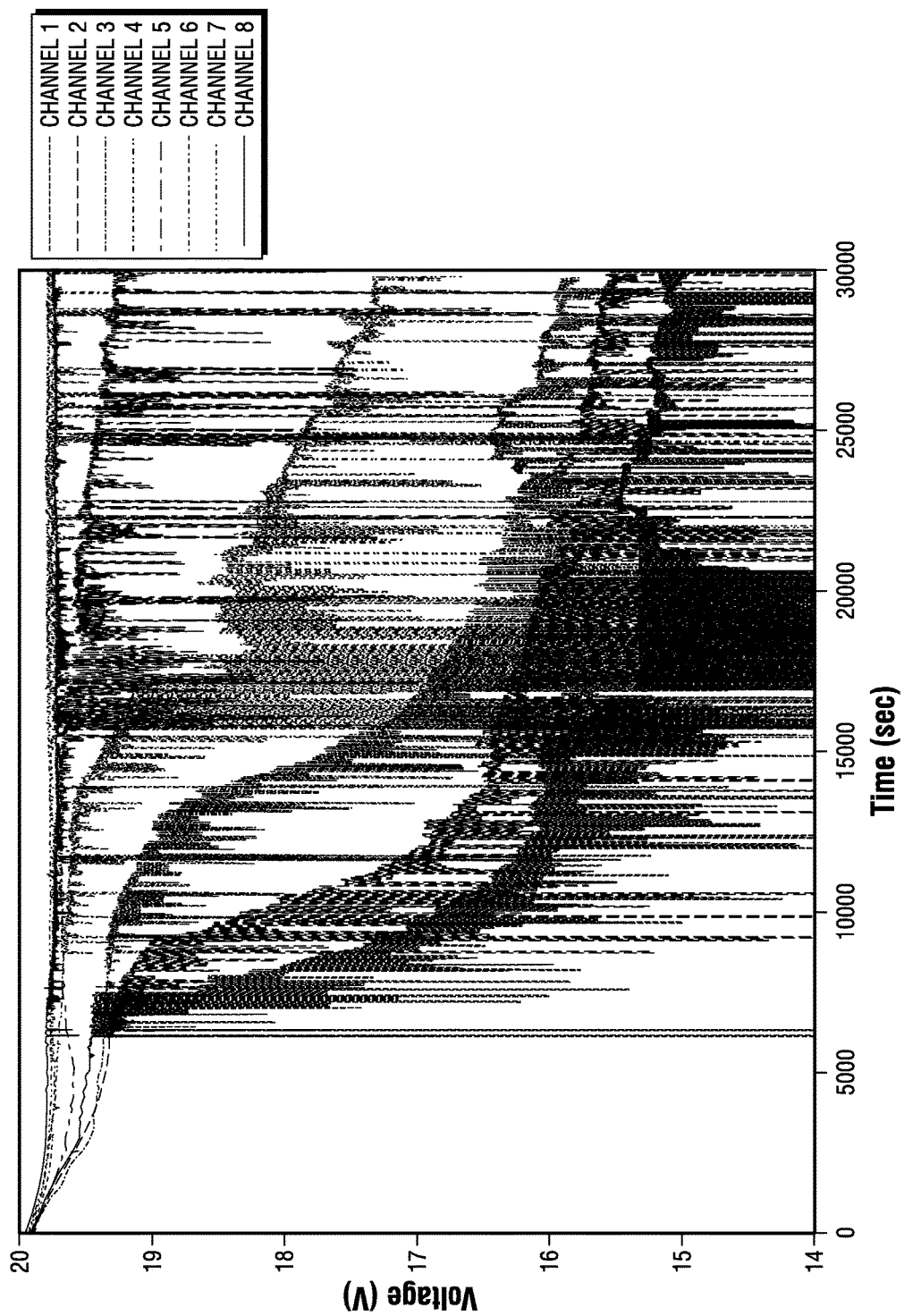
FIG. 9A illustrates a chart of time (seconds) versus voltage (V) for a prototype interface cell with eight (8) capacitance/conductance probes for 20% deionized water in heavy API crude oil emulsion according to an embodiment of the present invention.
Figure 9B:
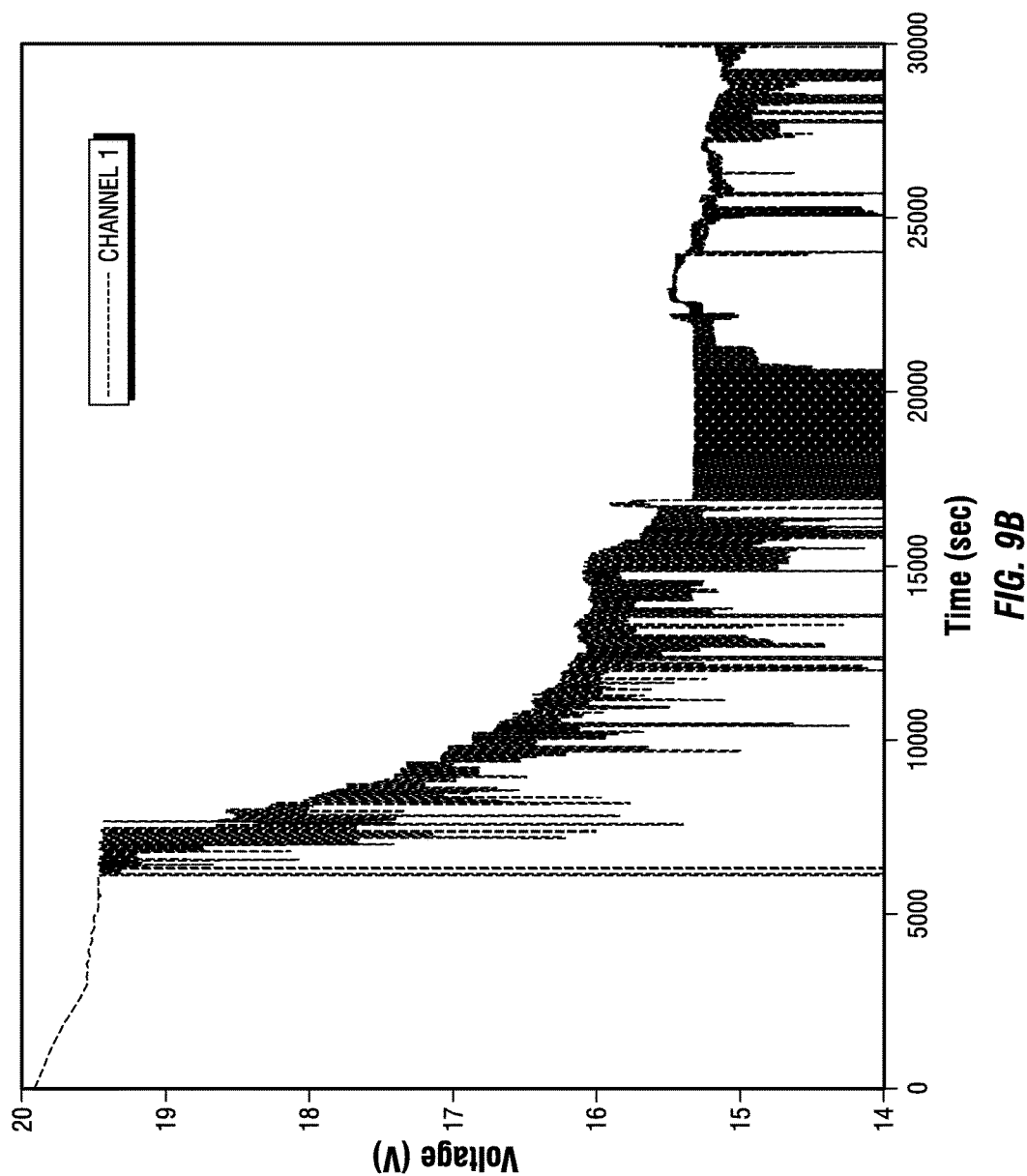
FIG. 9B illustrates a chart of time (seconds) versus voltage (V) for channel 1 of a prototype interface cell with eight (8) capacitance/conductance probes for 20% deionized water in heavy API crude oil emulsion according to an embodiment of the present invention.
Figure 9C:
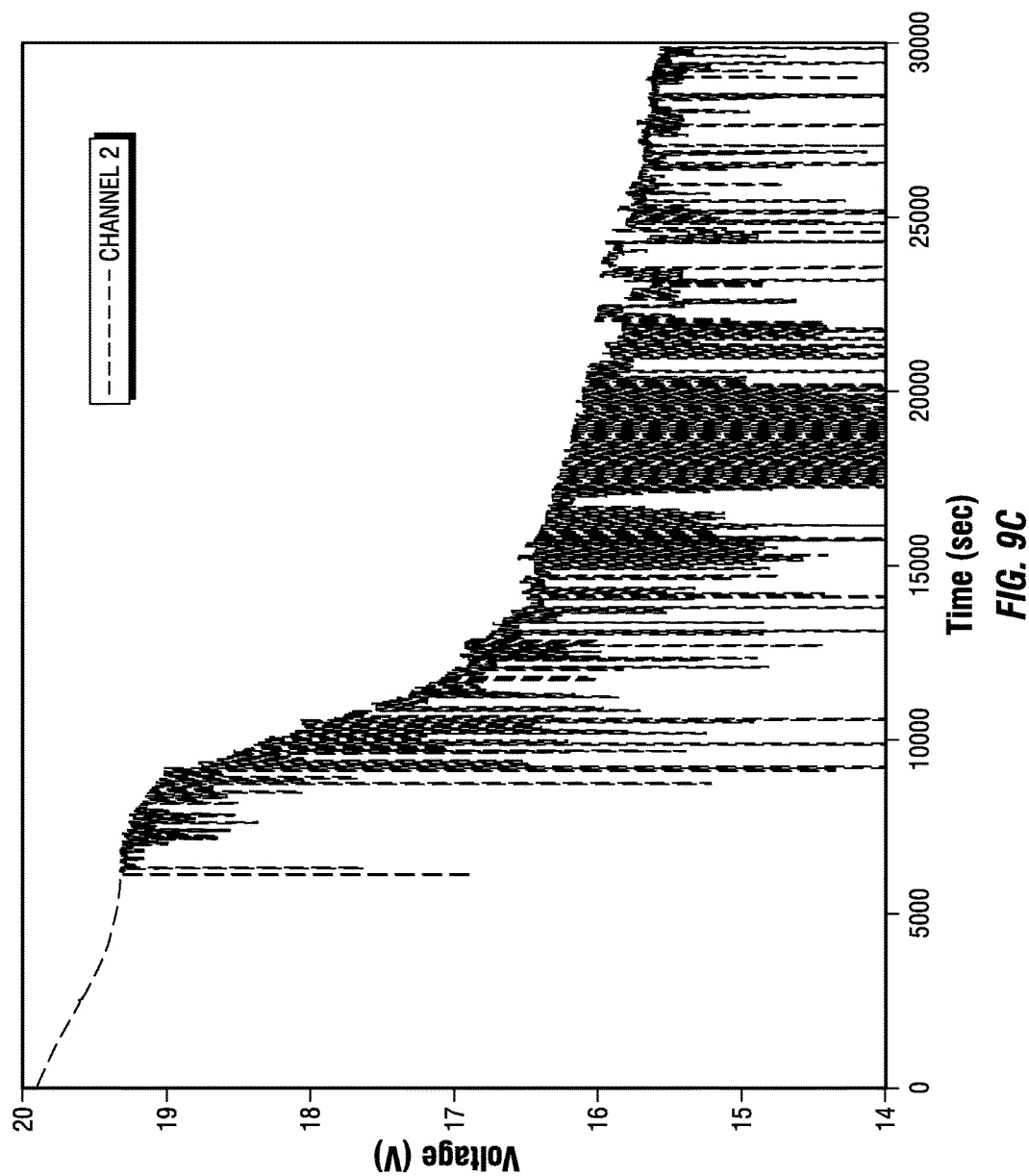
FIG. 9C illustrates a chart of time (seconds) versus voltage (V) for channel 2 of a prototype interface cell with eight (8) capacitance/conductance probes for 20% deionized water in heavy API crude oil emulsion according to an embodiment of the present invention.
Figure 9D:
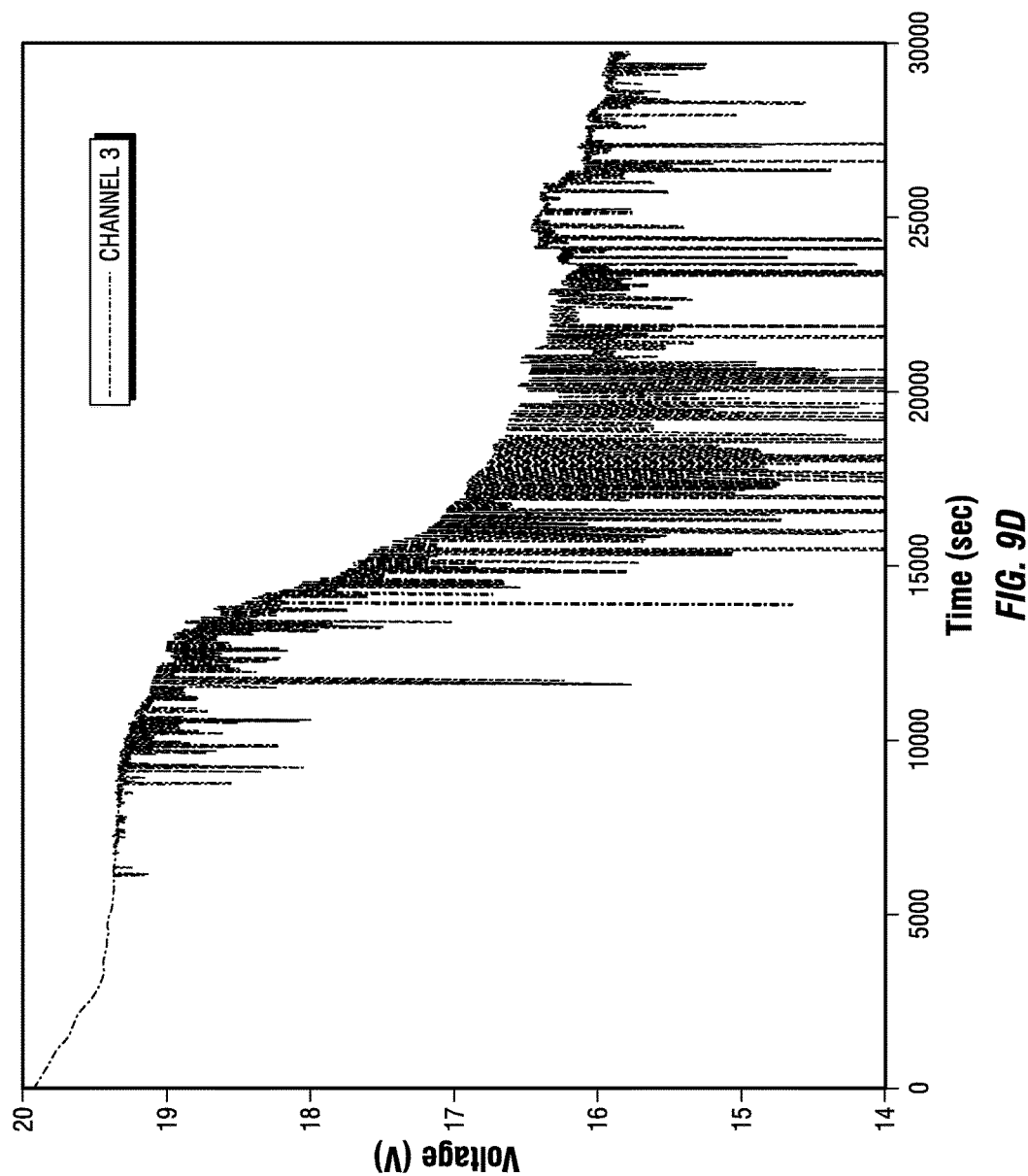
FIG. 9D illustrates a chart of time (seconds) versus voltage (V) for channel 3 of a prototype interface cell with eight (8) capacitance/conductance probes for 20% deionized water in heavy API crude oil emulsion according to an embodiment of the present invention.
Figure 9E:
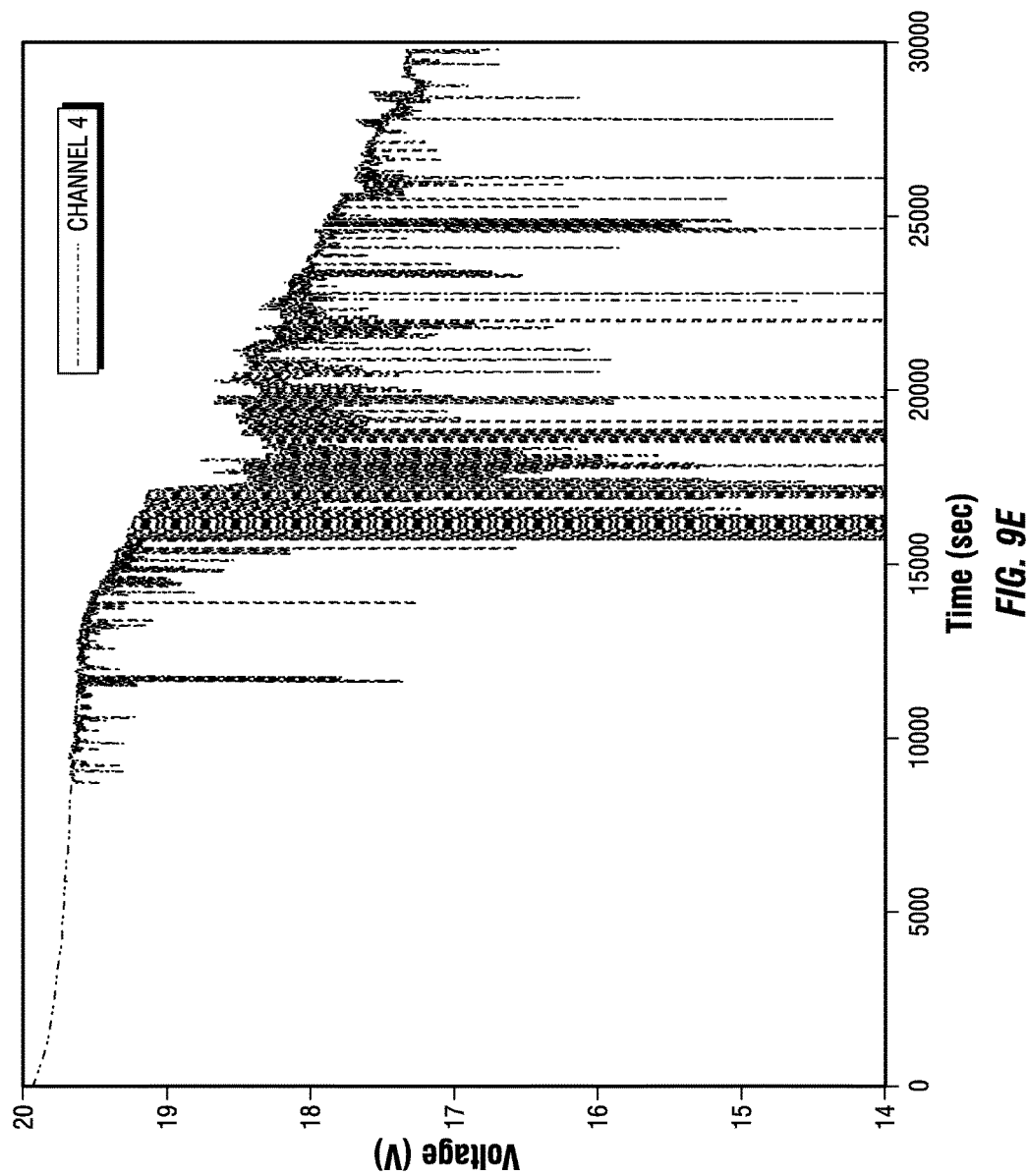
FIG. 9E illustrates a chart of time (seconds) versus voltage (V) for channel 4 of a prototype interface cell with eight (8) capacitance/conductance probes for 20% deionized water in heavy API crude oil emulsion according to an embodiment of the present invention.
Figure 9F:
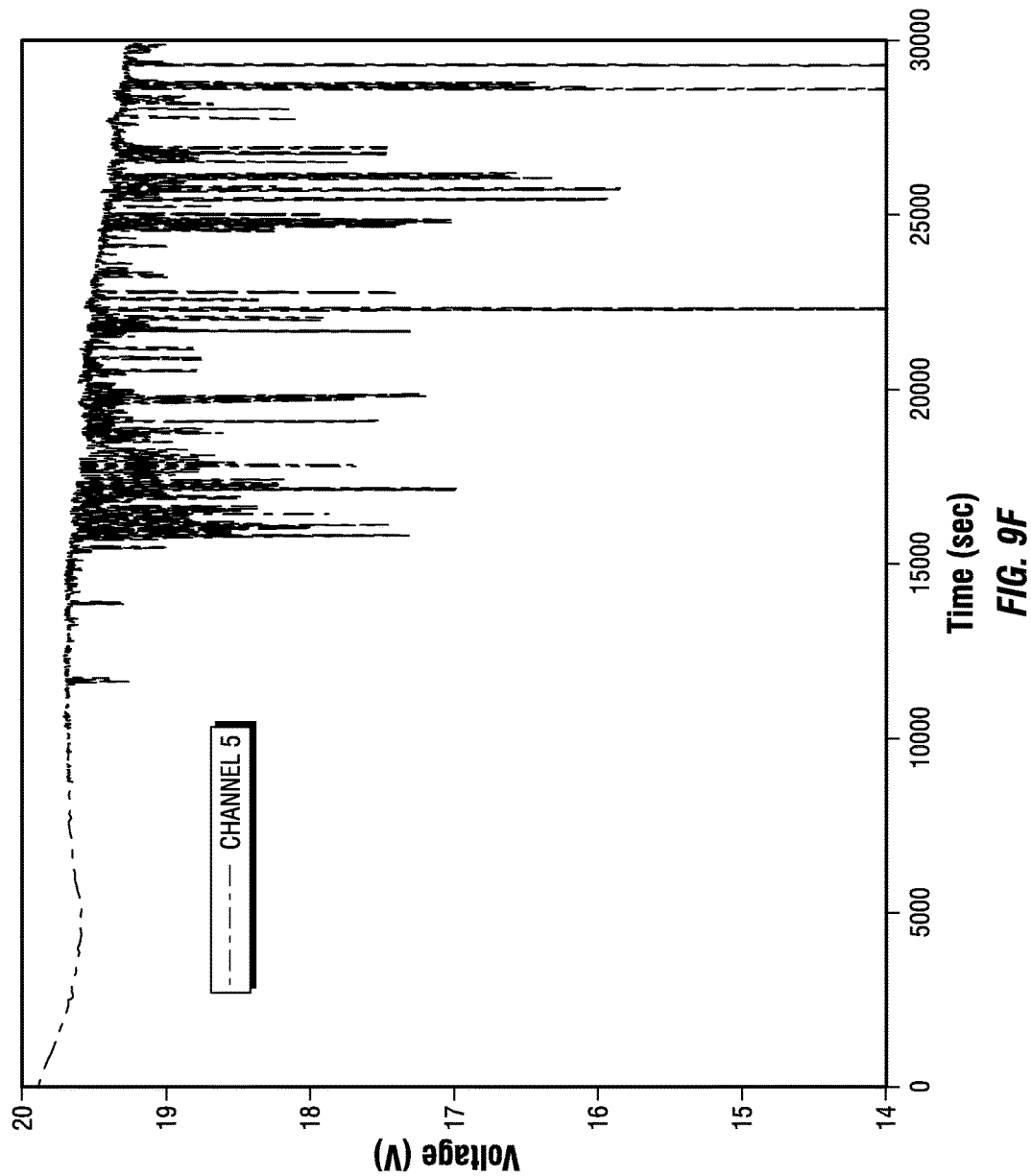
FIG. 9F illustrates a chart of time (seconds) versus voltage (V) for channel 5 of a prototype interface cell with eight (8) capacitance/conductance probes for 20% deionized water in heavy API crude oil emulsion according to an embodiment of the present invention.
Figure 9G:
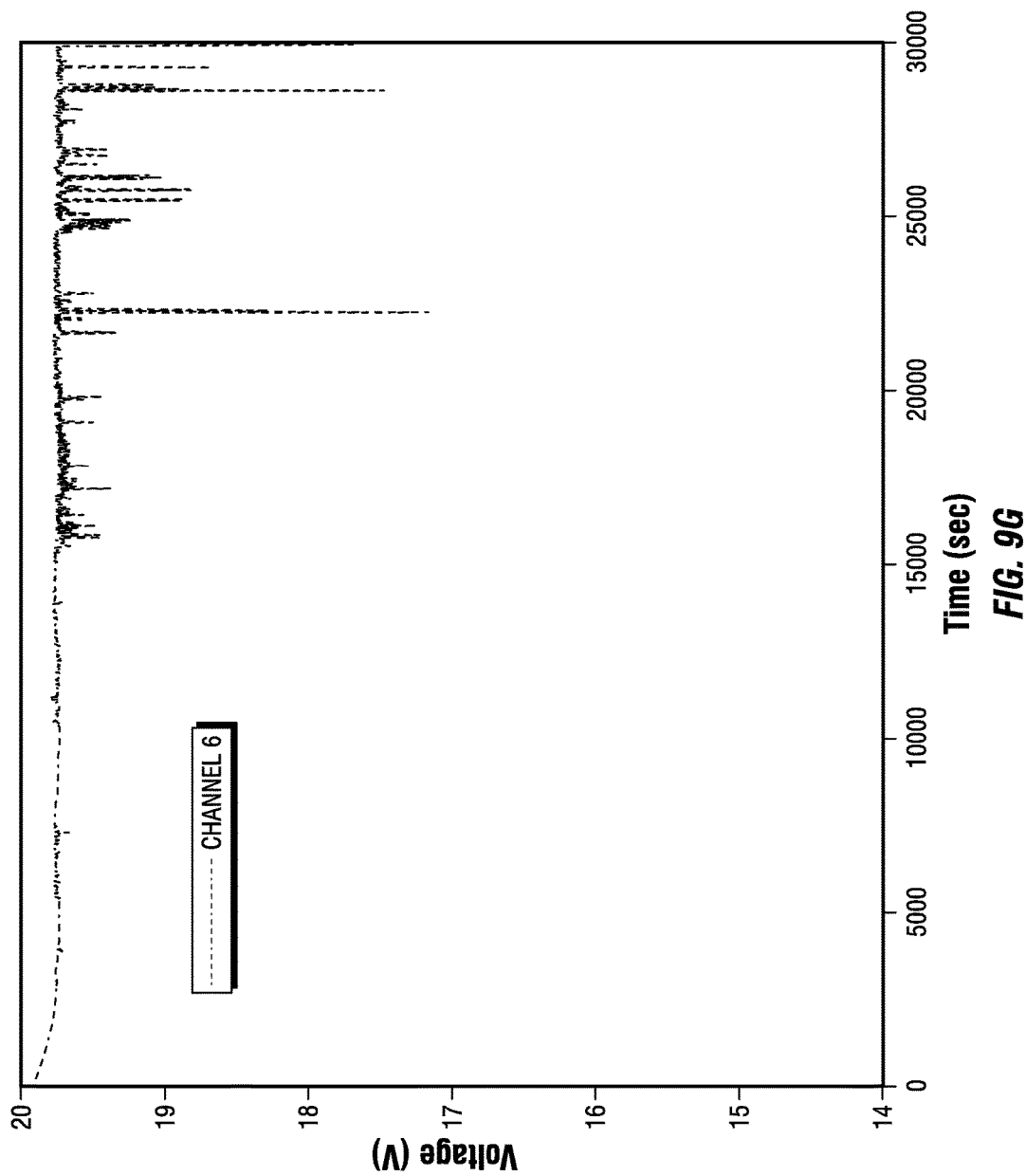
FIG. 9G illustrates a chart of time (seconds) versus voltage (V) for channel 6 of a prototype interface cell with eight (8) capacitance/conductance probes for 20% deionized water in heavy API crude oil emulsion according to an embodiment of the present invention.
Figure 9H:
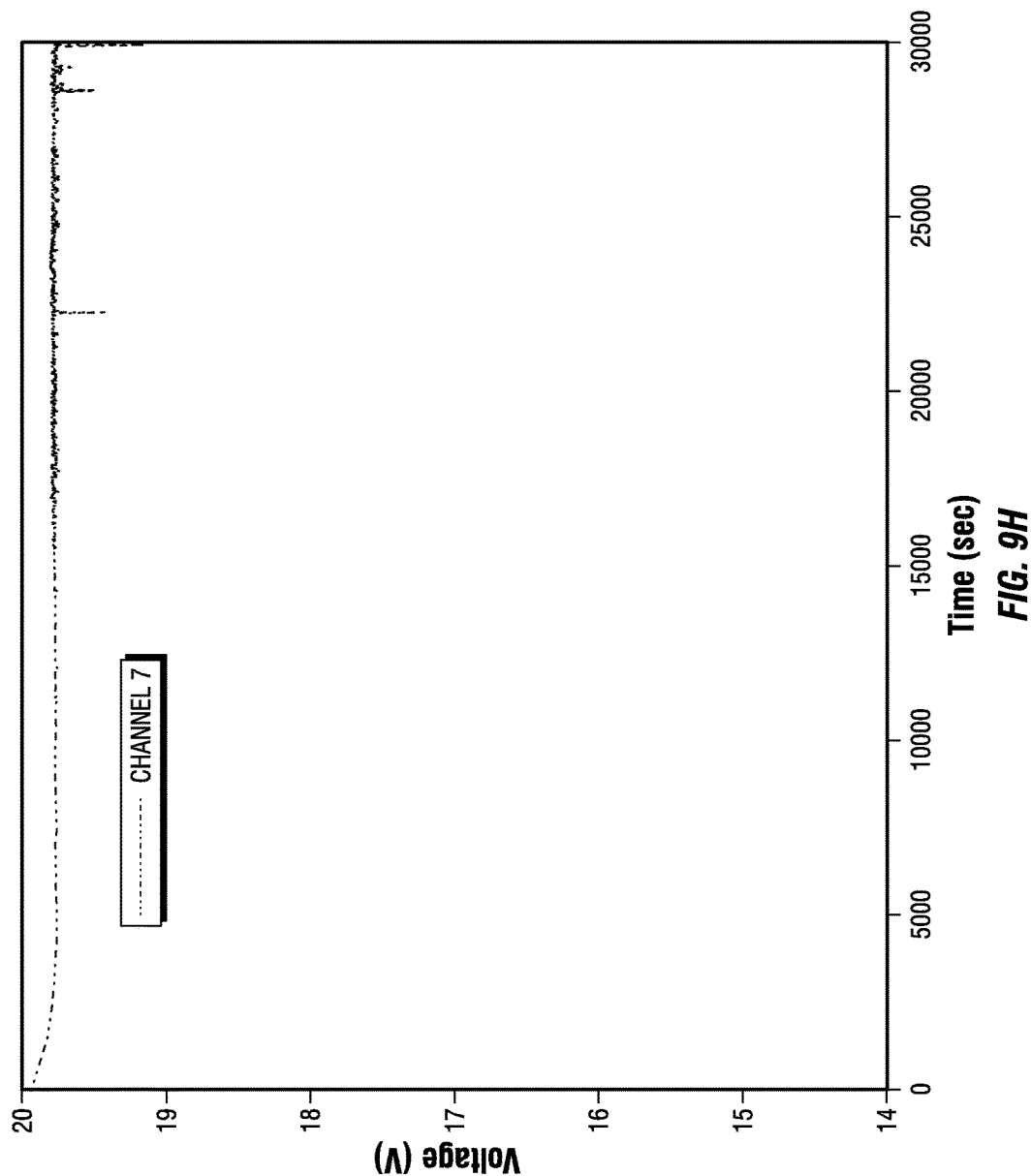
FIG. 9H illustrates a chart of time (seconds) versus voltage (V) for channel 7 of a prototype interface cell with eight (8) capacitance/conductance probes for 20% deionized water in heavy API crude oil emulsion according to an embodiment of the present invention.
Figure 9I:
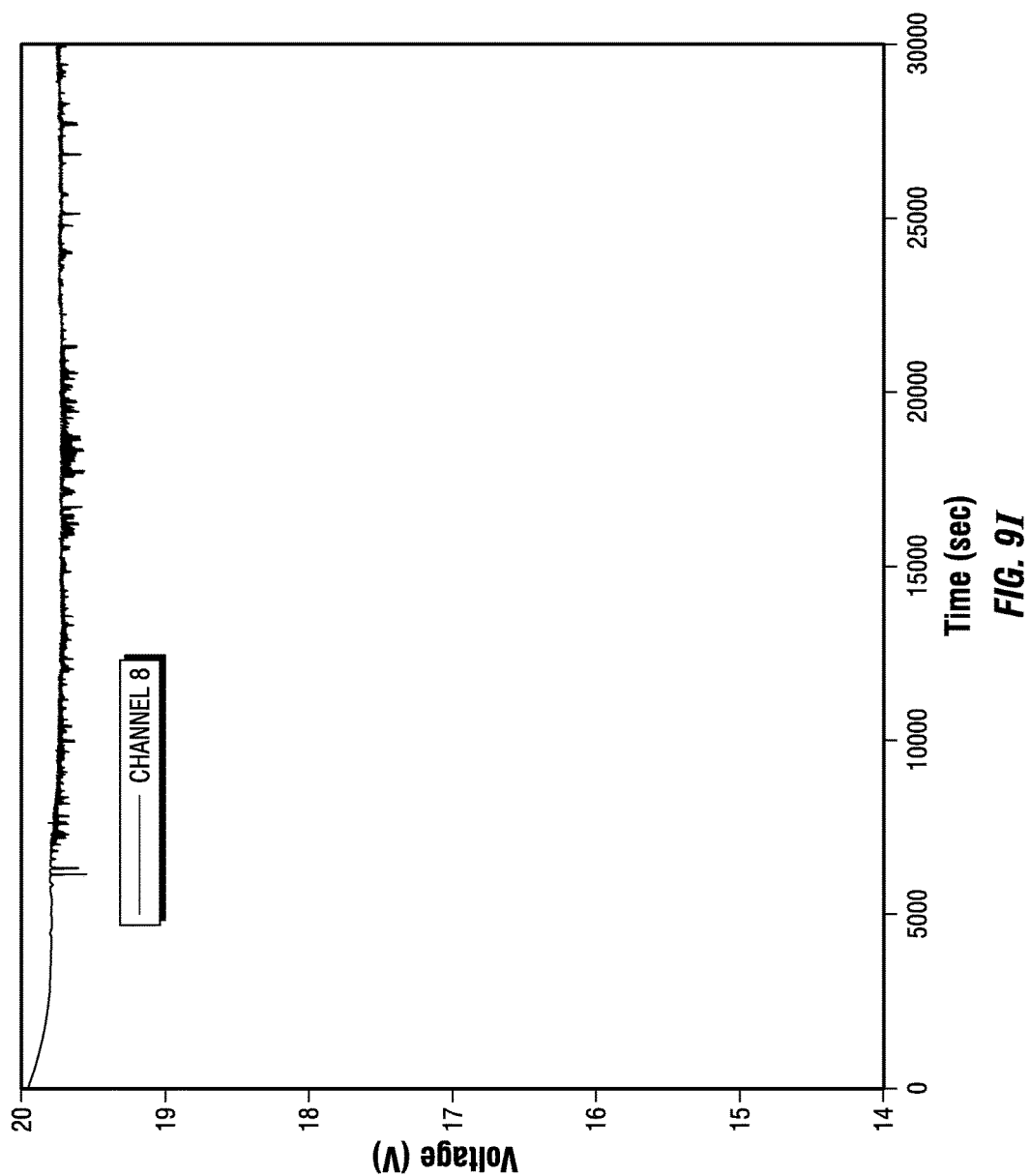
FIG. 9I illustrates a chart of time (seconds) versus voltage (V) for channel 8 of a prototype interface cell with eight (8) capacitance/conductance probes for 20% deionized water in heavy API crude oil emulsion according to an embodiment of the present invention.

FIG. 7 shows a flow chart for a method of measuring separation rate of water from water-in-crude oil emulsions 700 in a fluid stream. A first step 701 of the method includes measuring conductivity of two or more capacitance/conductance probes 206 disposed at different heights from the inner bottom surface of the interface cell 112. In an embodiment, the computing device 300 of the analyzer 114 receives a first signal indicative of conductivity from two or more probes 206 of the interface cell 112.

For example, FIGS. 8A through 8I and 9A through 9I represent raw data (e.g., Time vs. Voltage) from eight (8) capacitance/conductance probes 206 disposed in an interface cell 112 at different heights from the inner bottom surface of the cell 112. The geometry of the cell 112 and the height of each probe 206 from the inner bottom surface of the cell 112 are known and can be used to determine the separation as an actual volume or as a fraction. For comparisons to bottle tests, a fractional value would be preferred. In FIGS. 8A through 8I and 9A through 9I, the lower channel numbers represent a position closer to the bottom of the cell 112, and a more conductive water layer. Obviously, the details of a signal and its relationship to conductance depend on configuration of the electronics.

A second step 702 of the method includes determining an approximate location of an oil-water interface based on conductivity data (e.g., Time vs. Voltage) from the capacitance/conductance probes 206 disposed in the interface cell 112 at different heights from the inner bottom surface of the cell 112. In an embodiment, the computing device 300 of the analyzer 114 determines an approximate location of an oil-water interface based on conductivity data (e.g., Time vs. Voltage) from the probes 206 disposed in the cell 112 at different heights from the inner bottom surface of the cell 112. In an embodiment, the computing device 300 of the analyzer 114 determines a time at which an oil-water interface passes a tip of a capacitance/conductance probe 206 based on conductivity data from the probe 206.

For example, two qualitatively different signal profiles relating to a location of an oil-water interface are possible depending on water conductivities for deionized water and two crude oils with different API gravities, as shown in FIGS. 8A through 8I and 9A through 9I. FIGS. 8A through 8I show a lower viscosity, more quickly separating emulsion with deionized water and high API crude oil; and FIGS. 9A through 9I show a higher viscosity more slowly separating emulsion with deionized water and low API crude oil.

Assuming that a tip of a capacitance/conductance probe 206 in an interface cell 112 is initially immersed in a spatial region corresponding to an emulsion, its conductivity signal will be initially constant with time followed by a rapid decrease in voltage when the probe is immersed in water. This rapid decrease is followed either by a relative minimum or a plateau.

For the emulsion shown in FIGS. 8A through 8I, the time when the relative minimum in signal was reached was the time used to determine the interface location. The plateau is observed when the water is conductive, (e.g., salt water) because water is the most conductive component in the interface cell 112. For the emulsion shown in FIGS. 9A through 9I, the time when the signal starts to rapidly decrease represents the time that is used to determine the interface location.

The choice of which feature to use is strictly based on convenience. In FIGS. 8A through 8I, if the time when the signal starts to rapidly decrease were used, then some capacitance/conductance probes 206 would be eliminated from consideration because the emulsion separated at a faster rate than the test could be started, and, thus, the bottom probes (i.e., lower channel numbers) were already in water. In FIGS. 9A through 9I, using the time when the relative minimum in signal is reached would be less precise because the relative minimum is spread out over a long time interval and also some of the probes had not reached the minimum. Clearly neither technique represents exactly where the oil-water interface is located; however the separation rate depends only on the slope from the data of time vs. water separation. Accordingly, as long as a consistent measure is chosen for a particular emulsion, the exact interface location is not important because the rate of separation is being measured.

A third step 703 includes determining separation data (e.g., Time vs. Water Volume or Water Fraction) based on an approximate location of an oil-water interface and the geometry of the interface cell 112. In an embodiment, the computing device 300 determines separation data based on the approximate location of the oil-water interface and the geometry of the cell 112. In an embodiment, the computing device 300 determines separation data based on the approximate location of the oil-water interface at discrete times and the geometry of the cell 112. As shown in FIGS. 10 and 12, separation data can be determined based on the time when the conductance changes as determined in the second step 702 and knowing the geometry of the cell 112 and the height of the tip of the probe 206 from the inner bottom surface of the cell 112.

Time vs. water separation data is typically described by a sigmoidal type of relationship—an induction period with little to no change in separation volume followed by an increase in separation volume that is reasonably approximated as being linear with time, followed by a plateau as the separation approaches completion. FIGS. 10 and 12 show little to no evidence of an induction period for the emulsion tested (i.e., deionized water and high API crude oil). In FIG. 10, the separation data was collected at a temperature of 195° F. (91° C.), and, in FIG. 12, the data was collected at a temperature of 255° F. (124° C.).

A fourth step 704 includes determining separation rate (i.e., slope) based on separation data (e.g., Time vs. Water Volume or Water Fraction) for the fluid stream 104. In an embodiment, the computing device 300 determines separation rate (i.e., slope) based on separation data (e.g., Time vs. Water Volume or Water Fraction) for the stream 104. As shown in FIGS. 10 and 12, separation rate can be determined based on the slope of the separation data (e.g., Time vs. Water Volume or Water Fraction) as determined in the third step 703 for the stream 104.

Figure 11A:
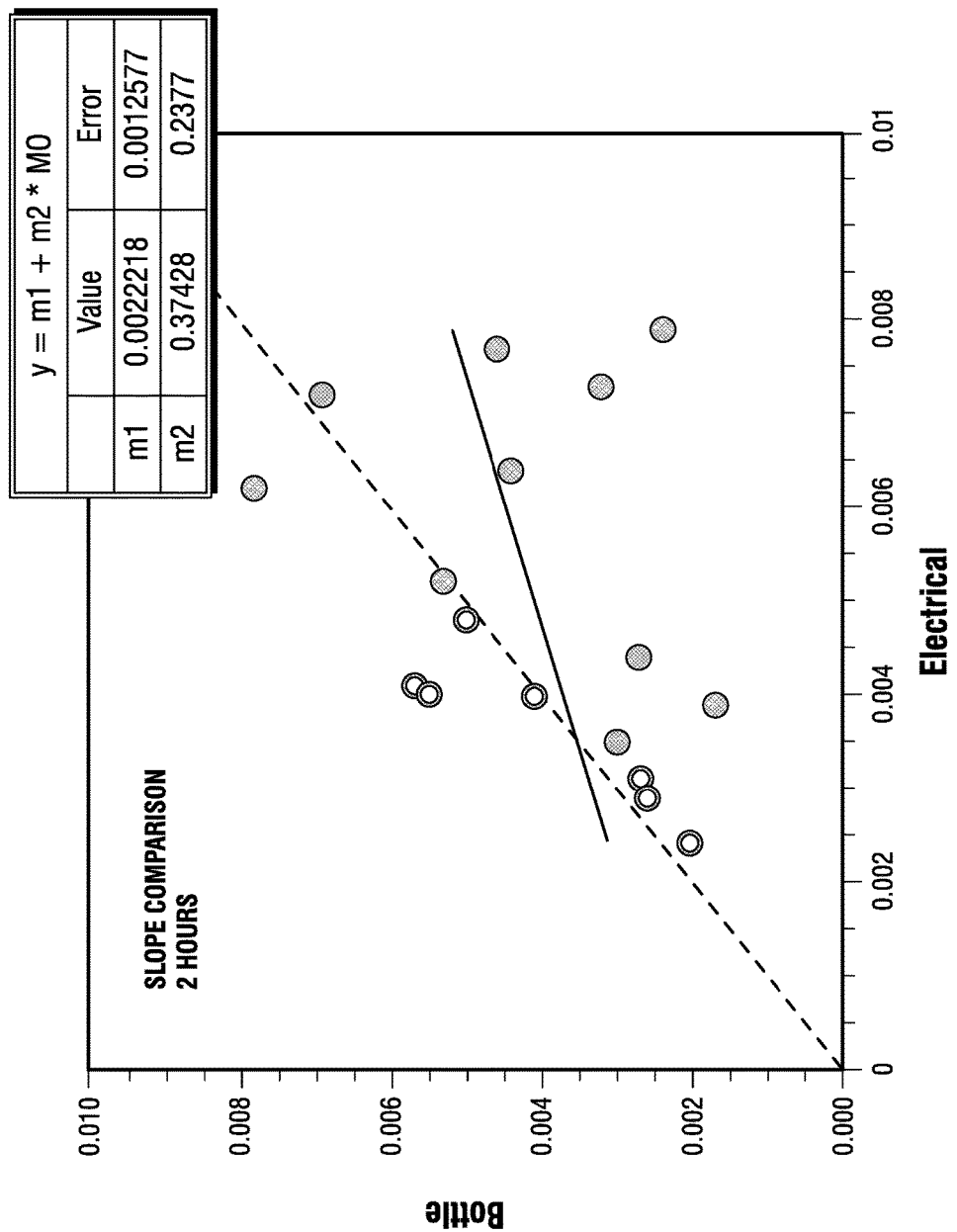
FIG. 11A illustrates a chart of slope of electrical conductivity tests (per minute) versus slope of bottle tests (per minute) for about two (2) (circles) or eight (8) (filled circles) hour separation of 20% deionized water in heavy API crude oil emulsion, showing a dotted line representing results if the slopes agreed with one another according to an embodiment of the present invention.
Figure 11B:
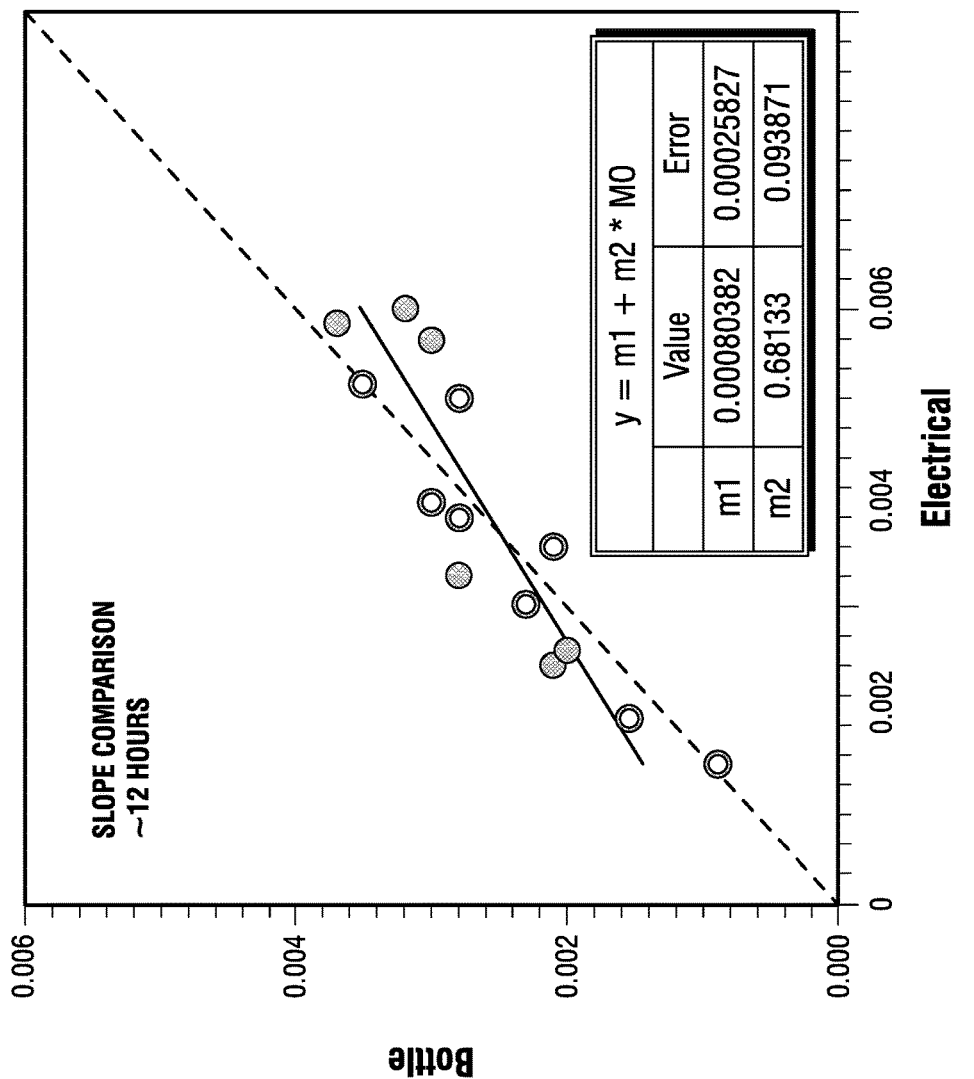
FIG. 11B illustrates a chart of slope of electrical conductivity tests (per minute) versus slope of bottle tests (per minute) for about eight (8) (filled circles) or twelve (12) (circles) hour separation of 20% deionized water in heavy API crude oil emulsion, showing a dotted line representing results if the slopes agreed with one another according to an embodiment of the present invention.
Figure 11C:
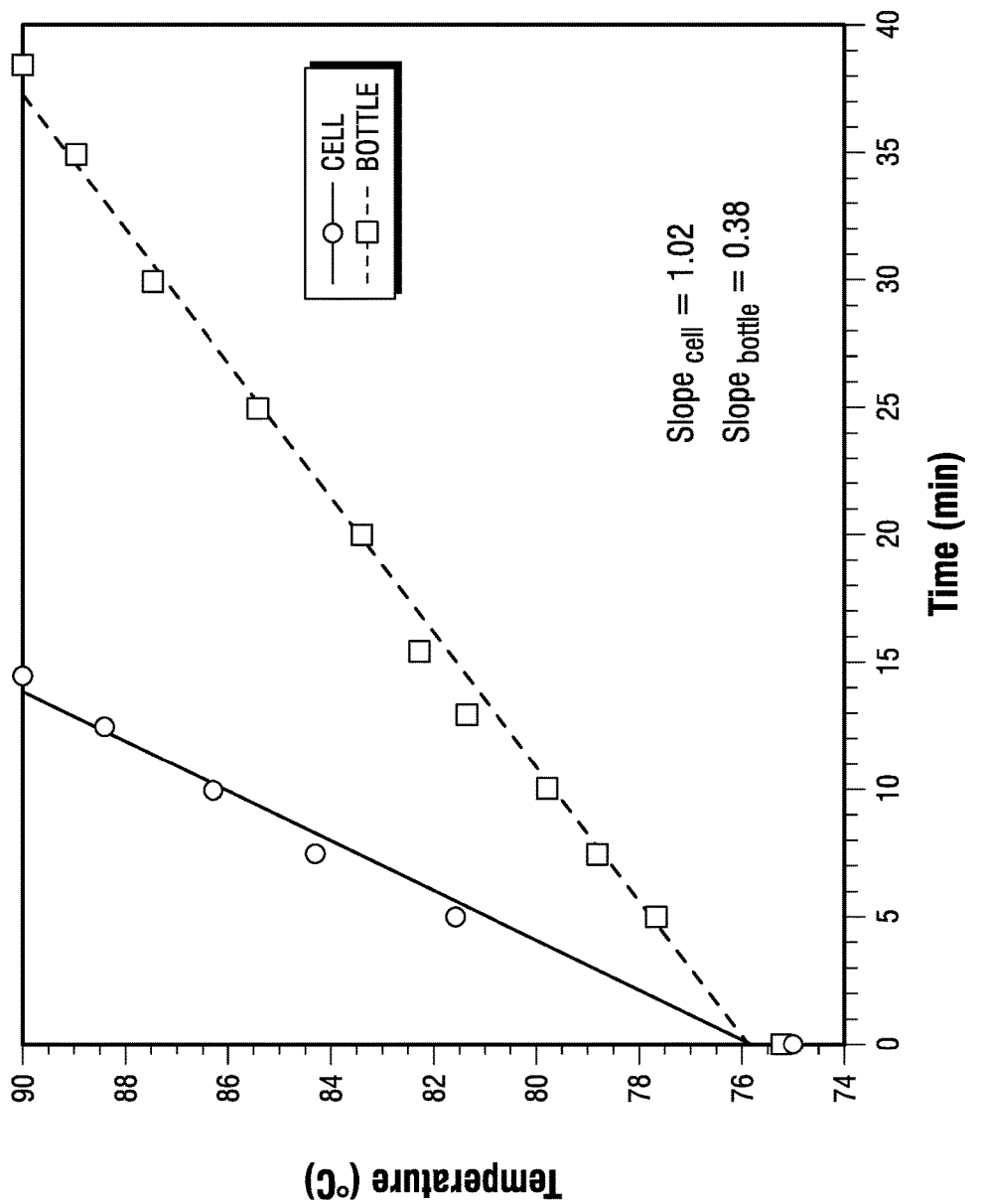
FIG. 11C illustrates a chart of time (minutes) versus temperature (° C.), showing electrical conductivity tests and bottle tests for 20% deionized water in heavy API crude oil emulsion according to an embodiment of the present invention.

FIG. 11 shows a comparison of the slopes of the lines for two types of data sets (slope of electrical conductivity tests vs. slope of bottle tests) for the heavy crude oil emulsion. A line x=y would indicate perfect agreement. As shown in FIG. 11, the agreement between the electrical conductivity tests (present invention) and the bottle tests is excellent. The data shown in FIG. 11 was collected at a temperature of 195° F. (91° C.).

In an embodiment, the method 700 optionally includes outputting conductivity data (e.g., Time vs. Voltage), separation data (Time vs. Water Volume or Water Fraction), and/or the separation rate (e.g., slope) for the fluid stream 104 to the presentation component 316, such as a display. In an embodiment, the method 700 optionally includes outputting a time at relative minimum in conductivity signal and/or a time at rapid decrease in conductivity signal for the stream 104 to the presentation component 316, such as a display.

In an embodiment, the method 700 optionally includes the step of measuring temperature of the fluid stream 104. In an embodiment, the temperature sensor 116 may be inserted directly into the fluid stream 104, as discussed above. In an embodiment, the computing device 300 receives a second signal indicative of temperature from the temperature sensor 116 for the stream 104, as discussed above. In an embodiment, the method 700 optionally includes outputting the temperature measured for the stream 104 to the presentation component 316, such as a display.

In an embodiment, the method 700 optionally includes the step of measuring pressure of the fluid stream 104. In an embodiment, the pressure sensor 124 may be inserted directly into the stream 104, as discussed above. In an embodiment, the computing device 300 receives a third signal indicative of pressure from the pressure sensor 124 for the stream 104, as discussed above. In an embodiment, the method 700 optionally includes outputting the pressure measured for the stream 104 to the presentation component 316, such as a display.

In an embodiment, the method 700 optionally includes the step of measuring flow rate of the fluid stream 104. In an embodiment, the flow meter 126 may be inserted directly into the stream 104, as discussed above. In an embodiment, the computing device 300 receives a fourth signal indicative of flow rate from the flow meter 126 for the stream 104, as discussed above. In an embodiment, the method 700 optionally includes outputting the flow rate measured for the stream 104 to the presentation component 316, such as a display.

In an embodiment, the method 700 includes a step of directing at least part of a water-in-crude oil emulsion source 102 to provide the fluid stream 104.

In an embodiment, the method 700 optionally includes the step of tagging the separation rate if flow rate of the fluid stream 104 is below a threshold value.

Laboratory Testing of Prototype Separation Rate Analyzer

A prototype system 100 including an interface cell 112, 500, an oven 118 and a computer 114 was constructed to evaluate the system 100 for measuring separation rate of water from water-in-crude oil emulsions and to compare those measured separation results to bottle tests used in a refinery.

A prototype interface cell 112, 500 was fabricated from carbon steel pipe and fittings. As shown in FIG. 4, eight (8) capacitance/conductance probes 206, 508 were used in the prototype interface cell 112, 500. In the prototype cell 112, 500, the probes 206, 508 were 1 mm tungsten welding rods for metal inert gas (MIG) welding applications. The probes 206, 508 were secured into place using a TEFLON® gland seal 506. After the two or more probes 206, 508 were positioned to a desired height from the inner surface of the cell 112, 500, the gland fitting 506 was screwed into a first prototype cover 504a and tightened to compress an inner TEFLON® seal. As shown in FIG. 4, TEFLON® tape was used on the threads. The first cover 504*a* (assembly) and the second cover 504*b* were screwed onto the chamber 502. As shown in FIG. 5, TEFLON® tape was used on the threads.

The prototype interface chamber 502 was constructed from carbon steel pipe with a diameter of about 1-inch (2.54 cm), a length of about 3-inches (7.5 cm) and a thickness of about ⅛-inch (0.3 cm) as depicted in FIGS. 4-6. The prototype cover 504 was constructed from a carbon steel pipe fitting sized to fit a 1-inch (2.54 cm) pipe.

In an embodiment, a plurality of interface cells 112, 500 may be piped/tubed in parallel to allow simultaneous measure of multiple samples. As illustrated in FIG. 6, five (5) prototype interface cells 112, 600 were disposed in an oven 118 in parallel to simultaneously measure multiple samples. As illustrated in FIGS. 10 & 12, four (4) prototype cells 112, 500 were used in parallel to simultaneously collect data from multiple samples.

For the laboratory evaluations of the interface cell 112, 500, mixtures of deionized water and crude oil used were prepared in a heated blender as the emulsions. The blender, deionized water and crude oil were pre-heated to about 70° C. About 20% deionized water in low API crude oil or about 20% deionized water in high API crude oil was blended at a reproducible, controlled speed.

The interface cell 112, 500, namely the interface cell chamber 202, 502 and cover 204, 504, was also pre-heated to about 70° C. The pre-heated emulsion was poured or pumped into the pre-heated interface chamber 202, 502. The cover 504 was screwed onto the emulsion-filled interface chamber 502, taking care not to short the capacitance/conductance probes 206, 404 against the carbon steel chamber 502.

The emulsion-filled interface cell 112, 500 was placed in an oven 118 and connected to a computing device 300 as discussed above. The cell 112, 500 was heated to a desired temperature. Typically, it takes about eighteen (18) minutes for about 195° F. (90° C.) and about forty-five (45) minutes for about 255° F. (125° C.) for the cell 112, 500 to reach the desired temperature. During heating to 255° F., the pressure inside the cell 112, 500 increased from about 0 psig to about 100 psig (i.e., about 101.4 kilopascals to about 790.8 kilopascals).

The electrical conductivity tests were started when the oven 118 reached the desired temperature (i.e., time=0). Typically, it takes about three and half (3.5) minutes for about 195° F. (90° C.) and about eleven (11) minutes for about 255° F. (125° C.).

The evaluations covered a range of conditions as follows:
1) about 195° F. to about 255° F. (i.e., about 90° C. to about 125° C.);
2) about 0 to about 100 psig (i.e., about 101.4 to about 790.8 kilopascals);
3) about 20% deionized water in low API crude oil (light crude oil emulsion) and about 20% deionized water in high API crude oil (heavy crude oil emulsion).

The inventors have shown that the conductance changes when an interface passes by a tip of a capacitance/conductance probe 206, 404. By using the time when the conductance changes in one of two predetermined manners (depends on the crude oil being used) and knowing the geometry of an interface cell 112, 500 and height of the tip of a capacitance/conductance probe 206, 404 from the bottom of the cell 112, 500, an approximate interface location can be determined. The resolution of the method relative to the interface height is determined by the number of capacitance/conductance probes 206, 404; six (6) are shown in FIG. 2 and eight (8) are shown in FIG. 4. The total number of probes 206, 404 is simply a function of the desired resolution and the geometry (size) of the cell.

A cylindrical interface cell 200, 500 is shown in FIGS. 2 & 4-6. As illustrated in FIG. 6, five (5) prototype interface cells 112, 600 were disposed in an oven 118 in parallel to simultaneously measure multiple samples. As illustrated in FIGS. 10 & 12, four (4) prototype interface cells 112, 500 were used in parallel to simultaneously collect data from multiple samples.

The non-obviousness of the system 100 arises from a number of issues. First, it was not clear whether the probes 206, 404 would become coated with debris from crude oil and, thus, render the readings unreliable. However, the comparison data shows that the bottle tests and the present invention agree at lower temperatures. Second, it was not obvious whether the small differences in height (e.g., about 0.1-inch (0.254 cm) apart as shown in FIG. 4) would allow for sufficient resolution. Although the present invention has some scatter, the interfacial levels vs. time approximate the bottle tests. Third, it was not obvious that a feature in the conductance vs. time signal could be used to reliably determine when the interface passed by a particular probe tip. Again, agreement with bottle tests suggests that the present invention would be reliable.

FIGS. 8A through 8I and 9A through 9I represent raw data from eight (8) capacitance/conductance probes 206, 404 disposed in an interface cell 112, 500 at different heights from the bottom of the cell 112, 500. The height of each capacitance/conductance probe is known in the interface cell 112, 500 and can be used to determine the separation as an actual volume or as a fraction. For comparison to bottle tests, a fractional value is preferred. In these figures, the lower channel numbers represent a position closer to the bottom of the cell 112, 500, and a more conductive water layer. Obviously, the details of a signal and its relationship to conductance depend on configuration of the electronics.

As shown in FIGS. 8A through 8I and 9A through 9I, two qualitatively different signal profiles relating to a location of an oil-water interface are possible depending on water conductivities for deionized water and two crude oils with different API gravities. FIGS. 8A through 8I show a lower viscosity, more quickly separating emulsion with deionized water and high API crude oil; and FIGS. 9A through 9I shows a higher viscosity, more slowly separating emulsion with deionized water and low API crude oil. Assuming that a tip of a capacitance/conductance probe 206, 404 in an interface cell 112, 500 is initially immersed in a spatial region corresponding to an emulsion, its conductivity signal will be initially constant with time followed by a rapid decrease in voltage when the probe is immersed in water. This rapid decrease is followed either by a relative minimum or a plateau. The minimum will be observed if the oil-water interface will be the highest conductive component (e.g., higher than pure water, pure oil or water-in-oil emulsion) in the cell. For the emulsion shown in FIGS. 8A through 8I, the time when the relative minimum signal was reached was the time used to determine the interface location. For the emulsion shown in FIGS. 9A through 9I, the time when the signal starts to rapidly decrease represents the time that is used to determine the interface location.

The choice of which feature to use is strictly based on convenience. In FIGS. 8A through 8I, if the time when the signal starts to rapidly decrease was used, then some capacitance/conductance probes 206, 404 would be eliminated from consideration because the emulsion separated at a faster rate than the test could be started, and, thus, the bottom probes (i.e., lower channel numbers) were already in water.

In FIGS. 9A through 9I, using the time when the relative minimum in signal is reached would be less precise because the relative minimum is spread out over a long time interval and also some of the probes had not reached the minimum. Clearly neither technique represents exactly where the oil-water interface is located; however, the separation rate depends only on the slope from the data of fractional separation vs. time. Accordingly, as long as a consistent measure is chosen for a particular emulsion, the exact interface location is not important.

Time vs. water separation data is typically described by a sigmoidal type of relationship—an induction period with little-to-no change in separation volume followed by an increase in separation volume that is reasonably approximated as being linear with time, followed by a plateau as the separation approaches completion. FIG. 10 shows little to no evidence of an induction period for the emulsion tested (i.e., deionized water and high API crude oil). Similar to bottle tests, the water separation data shown in FIG. 10 was collected at a temperature of 195° F. (91° C.). However, the emulsifying conditions were adjusted so that oil-water separation took no longer than about eight (8) hours for comparison of electrical conductivity tests to bottle tests which are typically performed by a person during an eight hour shift.

FIG. 11 shows a comparison of the slopes of the lines for the two types of data sets (slope of electrical conductivity tests vs. slope of bottle tests) for the heavy crude oil emulsion. A line x=y would indicate perfect agreement. As shown in FIG. 11, the agreement between the electrical conductivity tests and the bottle tests is excellent. The data shown in FIG. 11 was collected at a temperature of 195° F. (91° C.).

Similar to FIG. 10, FIG. 12 shows little to no evidence of an induction period for the heavy crude oil. However, unlike FIG. 10, the water separation data shown in FIG. 12 was collected at a temperature of 255° F. (124° C.). As compared to FIG. 10, FIG. 12 shows no degradation in the quality of the data. Because bottle tests cannot be performed safely at temperatures above 195° F. (91° C.), corresponding bottle test data could not be obtained at a temperature of 255° F. (124° C.). Depending on materials of construction for the interface cell 112, 500, elevated temperatures of hundreds of degrees Fahrenheit should be possible with the present invention.

The embodiments and examples set forth herein are presented to best explain the present invention and its practical application and to thereby enable those skilled in the art to make and utilize the invention. However, those skilled in the art will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims. The invention is specifically intended to be as broad as the claims below and their equivalents.

Definitions

As used herein, the terms "a," "an," "the," and "said" means one or more, unless the context dictates otherwise.

As used herein, the term "about" means the stated value plus or minus a margin of error or plus or minus 10% if no method of measurement is indicated.

As used herein, the term "or" means "and/or" unless explicitly indicated to refer to alternatives only or if the alternatives are mutually exclusive.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise," provided above.

As used herein, the terms "having," "has," and "have" have the same open-ended meaning as "comprising," "comprises," and "comprise," provided above.

As used herein, the terms "including," "includes," and "include" have the same open-ended meaning as "comprising," "comprises," and "comprise," provided above.

As used herein, the phrase "consisting of" is a closed transition term used to transition from a subject recited before the term to one or more material elements recited after the term, where the material element or elements listed after the transition term are the only material elements that make up the subject.

As used herein, the term "simultaneously" means occurring at the same time or about the same time, including concurrently.

INCORPORATION BY REFERENCE

All patents and patent applications, articles, reports, and other documents cited herein are fully incorporated by reference to the extent they are not inconsistent with this invention, as follows:

1) J. van Dijk, et al., *Monitoring the demulsification of crude oil emulsions by using conductivity measurements*, EMULSIONS AND EMULSION STABILITY; SURFACTANT SCIENCE Vol. 132 (CRC Press, 2d ed. Nov. 21, 2005); and
2) M. Kostoglou, et al., *Evolution of volume fractions and droplet sizes by analysis of electrical conductance curves during destabilization of oil-in-water emulsions,* 349(1) J. COLLOID INTERFACE SCI. (2010) 408-416.

What is claimed is:

1. A method, comprising:
    measuring electrolytic conductivity of two or more capacitance/conductance probes disposed in a fluid stream at different heights from an inner bottom surface of an interface cell having a known geometry;
    determining an approximate location of an oil-water interface based on conductivity data from the two or more capacitance/conductance probes;
    determining separation data for the fluid stream based on the approximate location of the oil-water interface and the known geometry of the interface cell; and
    determining a separation rate based on a slope of the separation data for the fluid stream.

2. The method of claim 1, wherein determining an approximate location comprises determining a time at which an oil-water interface passes a tip of each of the two or more capacitance/conductance probes.

3. The method of claim 2, wherein determining separation data comprises determining the separation data based on the approximate location of the oil-water interface at discrete times and the known geometry of the interface cell.

4. The method of claim 1, further comprising directing at least part of a water-in-crude-oil emulsion flow from an inlet to a desalter to provide the fluid stream or sample.

5. The method of claim 1, further comprising directing at least part of a water-in-crude-oil emulsion flow from an analyzer loop coupled in fluid communication with flow at a desalter to provide the fluid stream within the analyzer loop.

6. The method of claim 1, further comprising initiating conductivity measurements from the two or more capacitance/conductance probes when temperature of the fluid stream or sample is above a threshold value.

7. The method of claim 1, further comprising tagging the separation rate if pressure of the fluid stream or sample is above a threshold value.

8. The method of claim 1, further comprising tagging the separation rate if flow rate of the fluid stream is below a threshold value.

9. The method of claim 1, further comprising outputting the separation rate to a display.

10. The method of claim 1,
wherein the interface cell comprises:
an interface chamber having a first base shape and a first height, wherein the first base shape is selected from the group consisting of square, rectangular, circular and ellipse; and
a first interface cell cover having a same first base shape as the interface cell chamber and a second height, wherein one or more holes extend through the first interface cover, wherein the first interface cell cover is fastened to the interface cell chamber;
the two or more capacitance/conductance probes are disposed through the one or more holes in the first interface cell cover;
the fluid stream comprises a water-in-crude oil emulsion, and
further comprising a computer for determining the separation rate of water from the water-in-crude-oil emulsion based on one or more signals received from the two or more capacitance/conductance probes disposed at different heights from an inner bottom surface of the interface cell.

11. The method of claim 10, wherein the interface chamber comprises:
an interface sleeve having a first end and a second end, wherein the first end has the same base shape as the first interface cover, the second end has a second base shape and a third height, wherein the second base shape is selected from the group consisting of square, rectangular, circular and ellipse; and
a second interface cell cover having the same second base shape as the second end of the interface cell sleeve and a fourth height, wherein the second interface cell cover is fastened to the second end of the interface cell sleeve.

12. The method of claim 11, wherein the second base shape is smaller than the first base shape such that the sides of the interface cell taper towards the second base shape.

13. The method of claim 10, wherein the interface cell chamber and the first interface cell cover are constructed from a metal, a plastic or a combination thereof.

14. The method of claim 10, wherein the interface cell chamber and the first interface cell cover are constructed from a metal selected from the group consisting of carbon steel, stainless steel, stainless steel alloys and combinations thereof.

15. The method of claim 10, wherein the interface cell chamber and the first interface cell cover are constructed of a plastic selected from the group consisting of polyether ketone (PEEK), polymethylene, polytetrafluorethylene (PTFE), other high-temperature polymers and combinations thereof.

16. The method of claim 10, wherein the interface cell chamber and the first interface cell cover are constructed from carbon steel pipe and fittings.

17. The method of claim 1, wherein the capacitance/conductance probes are constructed from a conductive metal.

18. The method of claim 17, wherein the conductive metal is selected from the group consisting of aluminum, copper, nickel, silver, tungsten, zinc, and combinations thereof.

19. The method of claim 1, wherein the capacitance/conductance probes are constructed from 1 mm tungsten welding rods.

20. The method of claim 1, wherein the capacitance/conductance probes are spaced at about 0.1-inch (0.254 cm) apart.

21. The method of claim 10, wherein a first hole extends into the interface cell chamber from an outer, upper surface, a second hole opposing the first hole extends into the interface cell chamber from an outer, lower surface; wherein the first hole is fluidically connected to an inlet, and the second hole is fluidically connected to an outlet.

22. The method of claim 10, wherein the two or more capacitance/conductance probes are held in place with a metal fitting, a plastic fitting or a combination thereof.

23. The method of claim 10, wherein the two or more capacitance/conductance probes are held in place with a gland fitting.

24. The method of claim 10, wherein the two or more capacitance/conductance probes are held in place using an adhesive.

25. The method of claim 10, wherein the interface cell is disposed along an inlet to a desalter such that the fluid stream or sample contains at least a part of the water-in-crude-oil emulsion.

26. The method of claim 10, wherein the interface cell is disposed along an analyzer loop coupled in fluid communication with flow of a water-in-crude oil emulsion to produce the fluid stream within the analyzer loop.

27. The method of claim 10, further comprising a temperature sensor coupled to measure temperature of the fluid stream or sample, wherein the analyzer initiates a separation rate determination when the measured fluid stream or sample temperature reaches a target value.

28. The method of claim 10, further comprising a pressure sensor coupled to measure pressure of the fluid stream or sample, wherein the analyzer tags any determination of the separation rate in which the measured pressure is above a threshold value.

29. The method of claim 10, further comprising a flow meter coupled to measure flow rate of the fluid stream, wherein the analyzer tags any determination of the separation rate in which the measured flow rate is below a threshold value.

30. The method of claim 10, wherein the analyzer outputs the separation rate to a display.

* * * * *